(12) United States Patent
Garcia et al.

(10) Patent No.: US 8,298,244 B2
(45) Date of Patent: Oct. 30, 2012

(54) INTRACORPOREAL GRASPING DEVICE

(75) Inventors: Adrian Garcia, Los Gatos, CA (US);
Ting Tina Ye, San Jose, CA (US);
Quang Q Tran, Redwood City, CA
(US); Bart Bojanowski, San Jose, CA
(US); Alec Piplani, San Jose, CA (US);
Aaron Lee Berez, Menlo Park, CA (US)

(73) Assignee: Tyco Healtcare Group LP, Mansfield, MA (US)

( * ) Notice: Subject to any disclaimer, the term of this patent is extended or adjusted under 35 U.S.C. 154(b) by 0 days.

(21) Appl. No.: 12/877,808

(22) Filed: Sep. 8, 2010

(65) Prior Publication Data

US 2010/0331853 A1  Dec. 30, 2010

Related U.S. Application Data

(63) Continuation of application No. 11/924,369, filed on Oct. 25, 2007, now abandoned.

(60) Provisional application No. 60/854,439, filed on Oct. 26, 2006.

(51) Int. Cl.
*A61B 17/22* (2006.01)
*A61M 29/00* (2006.01)
(52) U.S. Cl. .................. 606/127; 606/198; 606/200
(58) Field of Classification Search .............. 600/37;
606/45–47, 51, 52, 106, 108, 110, 113, 115,
606/127, 128, 198, 200, 205, 207; 623/1.11
See application file for complete search history.

(56) References Cited

U.S. PATENT DOCUMENTS

| | | | |
|---|---|---|---|
| 3,996,938 A | 12/1976 | Clark, III |
| 4,046,150 A | 9/1977 | Schwartz et al. |
| 4,198,960 A | 4/1980 | Utsugi |
| 4,222,380 A | 9/1980 | Terayama |
| 4,299,225 A | 11/1981 | Glassman |
| 4,299,255 A | 11/1981 | Miller |
| 4,347,846 A | 9/1982 | Dormia |
| 4,611,594 A | 9/1986 | Grayhack et al. |
| 4,612,931 A | 9/1986 | Dormia |
| 4,625,726 A | 12/1986 | Duthoy |
| 4,650,466 A | 3/1987 | Luther |
| 4,655,771 A | 4/1987 | Wallsten |
| 4,727,873 A | 3/1988 | Mobin-Uddin |

(Continued)

FOREIGN PATENT DOCUMENTS

CA  2294484 A1  10/1999

(Continued)

OTHER PUBLICATIONS

US 6,056,761, May 2000, Gia et al. (withdrawn).

(Continued)

*Primary Examiner* — Ryan Severson
*Assistant Examiner* — Ashley Cronin
(74) *Attorney, Agent, or Firm* — Mark J. Kertz, Esq.

(57) ABSTRACT

An intracorporeal grasping device includes a tubular member for entering a lumen of a human body and the tubular member having a distal end portion. An elongated core member is disposed within the interior cavity of the tubular member for rotational or slidable movement within the tubular member and the elongated core member having a proximal end portion and a distal end portion. The elongated core member includes a grasping configuration for capturing an object (e.g., clot or debris) therein.

15 Claims, 17 Drawing Sheets

U.S. PATENT DOCUMENTS

| | | |
|---|---|---|
| 4,733,665 A | 3/1988 | Palmaz |
| 4,739,762 A | 4/1988 | Palmaz |
| 4,772,258 A | 9/1988 | Marangoni et al. |
| 4,790,812 A | 12/1988 | Hawkins et al. |
| 4,793,348 A | 12/1988 | Palmaz |
| 4,807,626 A | 2/1989 | McGirr |
| 4,850,957 A | 7/1989 | Summers |
| 4,873,978 A | 10/1989 | Ginsburg |
| 4,890,611 A | 1/1990 | Monfort et al. |
| 4,909,789 A | 3/1990 | Taguchi |
| 5,064,428 A | 11/1991 | Cope et al. |
| 5,071,407 A | 12/1991 | Termin et al. |
| 5,100,423 A | 3/1992 | Fearnot |
| 5,102,417 A | 4/1992 | Palmaz |
| 5,168,593 A | 12/1992 | Poje et al. |
| 5,171,233 A | 12/1992 | Amplatz et al. |
| 5,190,058 A | 3/1993 | Jones et al. |
| 5,192,286 A | 3/1993 | Phan et al. |
| 5,195,984 A | 3/1993 | Schatz |
| 5,197,978 A | 3/1993 | Hess |
| 5,211,636 A | 5/1993 | Mische |
| 5,217,468 A | 6/1993 | Clement |
| 5,222,971 A | 6/1993 | Willard et al. |
| 5,297,310 A | 3/1994 | Cox et al. |
| 5,300,086 A | 4/1994 | Gory et al. |
| 5,330,482 A | 7/1994 | Gibbs et al. |
| 5,342,371 A | 8/1994 | Welter et al. |
| 5,354,295 A | 10/1994 | Guglielmi et al. |
| 5,370,653 A | 12/1994 | Cragg |
| 5,387,219 A | 2/1995 | Rappe |
| 5,407,807 A | 4/1995 | Markus |
| 5,411,549 A | 5/1995 | Peters |
| 5,423,829 A | 6/1995 | Pham et al. |
| 5,456,667 A | 10/1995 | Ham et al. |
| 5,490,859 A | 2/1996 | Mische et al. |
| 5,496,330 A | 3/1996 | Bates et al. |
| 5,501,694 A | 3/1996 | Ressemann et al. |
| 5,527,326 A | 6/1996 | Hermann et al. |
| 5,535,756 A | 7/1996 | Parasher |
| 5,540,707 A | 7/1996 | Ressemann et al. |
| 5,569,245 A | 10/1996 | Guglielmi et al. |
| 5,571,122 A | 11/1996 | Kelly et al. |
| 5,573,520 A | 11/1996 | Schwartz |
| 5,573,547 A | 11/1996 | LeVeen et al. |
| 5,620,415 A | 4/1997 | Lucey et al. |
| 5,624,449 A | 4/1997 | Pham et al. |
| 5,645,075 A | 7/1997 | Palmer et al. |
| 5,665,098 A | 9/1997 | Kelly et al. |
| 5,669,933 A | 9/1997 | Simon et al. |
| 5,681,335 A | 10/1997 | Serra et al. |
| 5,683,401 A | 11/1997 | Schmieding et al. |
| 5,688,234 A | 11/1997 | Frisbie |
| 5,690,667 A | 11/1997 | Gia |
| 5,695,519 A | 12/1997 | Summers et al. |
| 5,702,413 A | 12/1997 | Lafontaine |
| 5,709,704 A | 1/1998 | Nott et al. |
| 5,720,764 A | 2/1998 | Naderlinger |
| 5,743,905 A | 4/1998 | Eder et al. |
| 5,749,883 A | 5/1998 | Halpern |
| 5,759,192 A | 6/1998 | Saunders |
| 5,762,069 A | 6/1998 | Kelleher et al. |
| 5,769,882 A | 6/1998 | Fogarty et al. |
| 5,779,716 A | 7/1998 | Cano et al. |
| 5,782,848 A | 7/1998 | Lennox |
| 5,792,145 A | 8/1998 | Bates et al. |
| 5,792,157 A | 8/1998 | Mische et al. |
| 5,800,454 A | 9/1998 | Jacobsen et al. |
| 5,800,520 A | 9/1998 | Fogarty et al. |
| 5,800,525 A | 9/1998 | Bachinski et al. |
| 5,814,064 A | 9/1998 | Daniel et al. |
| 5,824,037 A | 10/1998 | Fogarty et al. |
| 5,827,304 A | 10/1998 | Hart |
| 5,836,868 A | 11/1998 | Ressemann et al. |
| 5,846,248 A | 12/1998 | Chu et al. |
| 5,848,964 A | 12/1998 | Samuels |
| 5,851,206 A | 12/1998 | Guglielmi et al. |
| 5,882,329 A | 3/1999 | Patterson et al. |
| 5,891,128 A | 4/1999 | Gia et al. |
| 5,895,398 A | 4/1999 | Wensel et al. |
| 5,895,400 A | 4/1999 | Abela |
| 5,897,537 A | 4/1999 | Berg et al. |
| 5,897,567 A | 4/1999 | Ressemann et al. |
| 5,902,263 A | 5/1999 | Patterson et al. |
| 5,904,698 A | 5/1999 | Thomas et al. |
| 5,908,435 A | 6/1999 | Samuels |
| 5,911,717 A | 6/1999 | Jacobsen et al. |
| 5,911,734 A | 6/1999 | Tsugita et al. |
| 5,913,895 A | 6/1999 | Burpee et al. |
| 5,916,235 A | 6/1999 | Guglielmi |
| 5,925,061 A | 7/1999 | Ogi et al. |
| 5,928,261 A | 7/1999 | Ruiz |
| 5,935,139 A | 8/1999 | Bates |
| 5,941,869 A | 8/1999 | Patterson et al. |
| 5,944,728 A | 8/1999 | Bates |
| 5,947,985 A | 9/1999 | Imran |
| 5,947,995 A | 9/1999 | Samuels |
| 5,948,016 A | 9/1999 | Jang |
| 5,954,743 A | 9/1999 | Jang |
| 5,964,797 A | 10/1999 | Ho |
| 5,968,057 A | 10/1999 | Taheri |
| 5,972,019 A | 10/1999 | Engelson et al. |
| 5,976,131 A | 11/1999 | Guglielmi |
| 5,980,514 A | 11/1999 | Kupiecki et al. |
| 5,984,929 A | 11/1999 | Bashiri et al. |
| 6,013,086 A | 1/2000 | Ouchi et al. |
| 6,013,093 A | 1/2000 | Nott et al. |
| 6,022,363 A | 2/2000 | Walker et al. |
| 6,027,520 A | 2/2000 | Tsugita et al. |
| 6,030,397 A | 2/2000 | Monetti et al. |
| 6,063,100 A | 5/2000 | Diaz et al. |
| 6,063,111 A | 5/2000 | Hieshima et al. |
| 6,066,149 A | 5/2000 | Samson et al. |
| 6,066,152 A | 5/2000 | Strauss et al. |
| 6,066,158 A | 5/2000 | Samson et al. |
| 6,077,260 A | 6/2000 | Wheelock et al. |
| 6,090,135 A | 7/2000 | Plaia et al. |
| 6,096,034 A | 8/2000 | Kupiecki et al. |
| 6,096,053 A | 8/2000 | Bates |
| 6,099,534 A * | 8/2000 | Bates et al. .................. 606/127 |
| 6,099,549 A | 8/2000 | Bosma et al. |
| 6,110,198 A | 8/2000 | Fogarty et al. |
| 6,123,714 A | 9/2000 | Gia et al. |
| 6,129,755 A | 10/2000 | Mathis et al. |
| 6,146,395 A | 11/2000 | Kanz et al. |
| 6,146,396 A | 11/2000 | Konya et al. |
| 6,156,061 A | 12/2000 | Wallace et al. |
| 6,165,178 A | 12/2000 | Bashiri et al. |
| 6,165,213 A | 12/2000 | Goicoechea et al. |
| 6,168,603 B1 | 1/2001 | Leslie et al. |
| 6,168,604 B1 | 1/2001 | Cano |
| 6,171,327 B1 | 1/2001 | Daniel et al. |
| 6,174,318 B1 | 1/2001 | Bates et al. |
| 6,179,857 B1 | 1/2001 | Diaz et al. |
| 6,179,859 B1 | 1/2001 | Bates et al. |
| 6,187,017 B1 | 2/2001 | Gregory, Jr. |
| 6,190,394 B1 | 2/2001 | Lind et al. |
| 6,193,745 B1 | 2/2001 | Fogarty et al. |
| 6,203,552 B1 | 3/2001 | Bagley et al. |
| 6,214,025 B1 | 4/2001 | Thistle et al. |
| 6,221,039 B1 | 4/2001 | Durgin et al. |
| 6,238,412 B1 | 5/2001 | Dubrul et al. |
| 6,241,746 B1 | 6/2001 | Bosma et al. |
| 6,245,089 B1 | 6/2001 | Daniel et al. |
| 6,254,571 B1 | 7/2001 | Hart |
| 6,254,628 B1 | 7/2001 | Wallace et al. |
| 6,264,663 B1 | 7/2001 | Cano |
| 6,264,686 B1 | 7/2001 | Rieu |
| 6,264,687 B1 | 7/2001 | Tomonto |
| 6,267,777 B1 | 7/2001 | Bosma et al. |
| 6,273,900 B1 | 8/2001 | Nott et al. |
| 6,277,125 B1 | 8/2001 | Barry et al. |
| 6,277,126 B1 | 8/2001 | Barry et al. |
| 6,306,141 B1 | 10/2001 | Jervis |
| 6,312,463 B1 | 11/2001 | Rourke et al. |
| 6,319,242 B1 | 11/2001 | Patterson et al. |
| 6,325,807 B1 | 12/2001 | Que |
| 6,325,815 B1 | 12/2001 | Kusleika et al. |

| Patent Number | Date | Inventor(s) |
|---|---|---|
| 6,336,934 B1 | 1/2002 | Gilson et al. |
| 6,361,558 B1 | 3/2002 | Hieshima et al. |
| 6,379,329 B1 | 4/2002 | Naglreiter et al. |
| 6,383,205 B1 | 5/2002 | Samson et al. |
| 6,383,206 B1 | 5/2002 | Gillick et al. |
| 6,398,791 B1 | 6/2002 | Que et al. |
| 6,402,771 B1 | 6/2002 | Palmer et al. |
| 6,416,519 B1 | 7/2002 | VanDusseldorp |
| 6,425,893 B1 | 7/2002 | Guglielmi |
| 6,425,914 B1 | 7/2002 | Wallace et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,443,972 B1 | 9/2002 | Bosma et al. |
| 6,454,775 B1 | 9/2002 | Demarais et al. |
| 6,458,139 B1 | 10/2002 | Palmer et al. |
| 6,485,497 B2 | 11/2002 | Wensel et al. |
| 6,485,524 B2 | 11/2002 | Strecker |
| 6,491,719 B1 | 12/2002 | Fogarty et al. |
| 6,500,182 B2 | 12/2002 | Foster |
| 6,511,468 B1 | 1/2003 | Cragg et al. |
| 6,514,191 B1 | 2/2003 | Popowski et al. |
| 6,514,273 B1 | 2/2003 | Voss et al. |
| 6,520,968 B2 | 2/2003 | Bates et al. |
| 6,530,935 B2 | 3/2003 | Wensel et al. |
| 6,533,811 B1 | 3/2003 | Ryan et al. |
| 6,554,849 B1 | 4/2003 | Jones et al. |
| 6,572,648 B1 | 6/2003 | Klumb et al. |
| 6,575,997 B1 | 6/2003 | Palmer et al. |
| 6,592,607 B1 | 7/2003 | Palmer et al. |
| 6,596,005 B1 | 7/2003 | Kanz et al. |
| 6,602,265 B2 | 8/2003 | Dubrul et al. |
| 6,641,590 B1 | 11/2003 | Palmer et al. |
| 6,645,224 B2 | 11/2003 | Gilson et al. |
| 6,652,548 B2 | 11/2003 | Evans et al. |
| 6,656,214 B1 | 12/2003 | Fogarty et al. |
| 6,660,003 B1 | 12/2003 | DeVore et al. |
| 6,660,014 B2 | 12/2003 | Demarais et al. |
| 6,663,650 B2 | 12/2003 | Sepetka et al. |
| 6,673,106 B2 | 1/2004 | Mitelberg |
| 6,679,893 B1 | 1/2004 | Tran |
| 6,685,722 B1 | 2/2004 | Rosenbluth et al. |
| 6,692,508 B2 | 2/2004 | Wensel et al. |
| 6,692,509 B2 | 2/2004 | Wensel et al. |
| 6,702,782 B2 | 3/2004 | Miller et al. |
| 6,702,830 B1 | 3/2004 | Demarais et al. |
| 6,723,108 B1 | 4/2004 | Jones et al. |
| 6,730,104 B1 | 5/2004 | Sepetka et al. |
| 6,743,236 B2 | 6/2004 | Barry et al. |
| 6,749,619 B2 | 6/2004 | Ouriel et al. |
| 6,755,813 B2 | 6/2004 | Ouriel et al. |
| 6,811,560 B2 | 11/2004 | Jones et al. |
| 6,818,013 B2 | 11/2004 | Mitelberg |
| 6,824,545 B2 | 11/2004 | Sepetka et al. |
| 6,833,002 B2 | 12/2004 | Stack et al. |
| 6,833,003 B2 | 12/2004 | Jones et al. |
| 6,878,151 B2 | 4/2005 | Carrison et al. |
| 6,887,268 B2 | 5/2005 | Butaric et al. |
| 6,893,413 B2 | 5/2005 | Martin |
| 6,893,451 B2 | 5/2005 | Cano et al. |
| 6,902,540 B2 | 6/2005 | Dorros et al. |
| 6,913,612 B2 | 7/2005 | Palmer et al. |
| 6,921,414 B2 | 7/2005 | Klumb et al. |
| 6,929,634 B2 | 8/2005 | Dorros et al. |
| 6,939,353 B2 | 9/2005 | Que et al. |
| 6,945,977 B2 | 9/2005 | Demarais et al. |
| 6,953,468 B2 | 10/2005 | Jones et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 6,974,473 B2 | 12/2005 | Barclay et al. |
| 6,989,020 B2 | 1/2006 | Jones et al. |
| 7,001,422 B2 | 2/2006 | Escamilla |
| 7,004,954 B1 | 2/2006 | Voss et al. |
| 7,004,956 B2 | 2/2006 | Palmer et al. |
| 7,037,316 B2 | 5/2006 | McGuckin, Jr. et al. |
| 7,037,331 B2 | 5/2006 | Mitelberg et al. |
| 7,041,116 B2 | 5/2006 | Goto et al. |
| 7,052,500 B2 | 5/2006 | Bashiri et al. |
| 7,056,328 B2 | 6/2006 | Arnott |
| 7,058,456 B2 | 6/2006 | Pierce |
| 7,063,714 B2 | 6/2006 | Dorros et al. |
| 7,101,380 B2 | 9/2006 | Khachin et al. |
| 7,128,073 B1 | 10/2006 | van der Burg et al. |
| 7,129,276 B2 | 10/2006 | Ferrari |
| 7,147,659 B2 | 12/2006 | Jones |
| 7,156,871 B2 | 1/2007 | Jones et al. |
| 7,179,269 B2 | 2/2007 | Welch et al. |
| 7,179,273 B1 | 2/2007 | Palmer et al. |
| 7,182,774 B2 | 2/2007 | Barry et al. |
| 7,195,648 B2 | 3/2007 | Jones et al. |
| 7,201,769 B2 | 4/2007 | Jones et al. |
| 7,232,432 B2 | 6/2007 | Fulton, III et al. |
| 7,264,628 B2 | 9/2007 | Jones et al. |
| 7,270,674 B2 | 9/2007 | Jones et al. |
| 7,285,126 B2 | 10/2007 | Sepetka et al. |
| 7,294,123 B2 | 11/2007 | Jones et al. |
| 7,306,622 B2 | 12/2007 | Jones et al. |
| 7,309,351 B2 | 12/2007 | Escamilla et al. |
| 7,311,726 B2 | 12/2007 | Mitelberg et al. |
| 7,323,000 B2 | 1/2008 | Monstdt et al. |
| 7,344,500 B2 | 3/2008 | Talbot et al. |
| 7,344,550 B2 | 3/2008 | Carrison et al. |
| 7,344,558 B2 | 3/2008 | Lorenzo et al. |
| 7,357,809 B2 | 4/2008 | Jones et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,416,555 B2 | 8/2008 | Krivoruchko |
| 7,481,821 B2 | 1/2009 | Fogarty et al. |
| 7,510,565 B2 | 3/2009 | Gilson et al. |
| 7,517,352 B2 | 4/2009 | Evans et al. |
| 7,524,319 B2 | 4/2009 | Dubrul |
| 7,534,251 B2 * | 5/2009 | WasDyke ............... 606/200 |
| 7,534,252 B2 | 5/2009 | Sepetka et al. |
| 7,553,314 B2 | 6/2009 | Khachin et al. |
| 7,553,321 B2 | 6/2009 | Litzenberg et al. |
| 7,582,101 B2 | 9/2009 | Jones et al. |
| 2001/0041899 A1 | 11/2001 | Foster |
| 2001/0044649 A1 | 11/2001 | Vallana et al. |
| 2001/0053929 A1 | 12/2001 | Vonesh et al. |
| 2002/0082558 A1 | 6/2002 | Samson et al. |
| 2002/0193868 A1 | 12/2002 | Mitelberg |
| 2003/0153944 A1 | 8/2003 | Phung et al. |
| 2004/0059407 A1 | 3/2004 | Escamilla et al. |
| 2004/0078050 A1 | 4/2004 | Monstadt |
| 2004/0098025 A1 | 5/2004 | Sepetka et al. |
| 2004/0215222 A1 | 10/2004 | Krivoruchko |
| 2005/0021125 A1 | 1/2005 | Stack et al. |
| 2005/0033348 A1 | 2/2005 | Sepetka et al. |
| 2005/0049619 A1 | 3/2005 | Sepetka et al. |
| 2005/0059995 A1 | 3/2005 | Sepetka et al. |
| 2005/0085846 A1 * | 4/2005 | Carrison et al. ............... 606/200 |
| 2005/0085849 A1 | 4/2005 | Sepetka et al. |
| 2005/0119668 A1 | 6/2005 | Teague et al. |
| 2005/0124973 A1 | 6/2005 | Dorros et al. |
| 2005/0125024 A1 | 6/2005 | Sepetka et al. |
| 2005/0149111 A1 | 7/2005 | Kanazawa et al. |
| 2005/0165441 A1 | 7/2005 | McGuckin, Jr. et al. |
| 2005/0209678 A1 | 9/2005 | Henkes et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0267323 A1 | 12/2005 | Dorros et al. |
| 2005/0267491 A1 | 12/2005 | Kellett et al. |
| 2005/0277979 A1 | 12/2005 | Dorros et al. |
| 2005/0288686 A1 | 12/2005 | Sepetka et al. |
| 2006/0064114 A1 | 3/2006 | Obitsu et al. |
| 2006/0100571 A1 | 5/2006 | Venturelli |
| 2006/0184194 A1 | 8/2006 | Pal et al. |
| 2006/0195137 A1 | 8/2006 | Sepetka et al. |
| 2006/0224179 A1 | 10/2006 | Kucharczyk et al. |
| 2006/0287667 A1 | 12/2006 | Abela |
| 2007/0032816 A1 * | 2/2007 | O'Connell et al. ............ 606/200 |
| 2007/0038226 A1 | 2/2007 | Galdonik et al. |
| 2007/0179513 A1 | 8/2007 | Deutsch |
| 2007/0185500 A1 | 8/2007 | Martin et al. |

| | | | |
|---|---|---|---|
| 2007/0185501 A1 | 8/2007 | Martin et al. | |
| 2007/0191880 A1* | 8/2007 | Cartier et al. ............... 606/200 |
| 2007/0198029 A1 | 8/2007 | Martin et al. | |
| 2007/0198030 A1 | 8/2007 | Martin et al. | |
| 2007/0208367 A1 | 9/2007 | Fiorella et al. | |
| 2007/0208371 A1 | 9/2007 | French et al. | |
| 2007/0225749 A1 | 9/2007 | Martin et al. | |
| 2007/0288038 A1 | 12/2007 | Bimbo | |
| 2008/0027481 A1* | 1/2008 | Gilson et al. ............... 606/200 |
| 2008/0082107 A1 | 4/2008 | Miller et al. | |
| 2008/0119888 A1 | 5/2008 | Huffmaster | |
| 2008/0183185 A1 | 7/2008 | Miller et al. | |
| 2008/0183198 A1 | 7/2008 | Sepetka et al. | |
| 2008/0188865 A1 | 8/2008 | Miller et al. | |
| 2008/0262528 A1 | 10/2008 | Martin | |
| 2008/0262532 A1 | 10/2008 | Martin | |
| 2009/0069828 A1 | 3/2009 | Martin et al. | |
| 2009/0163851 A1 | 6/2009 | Holloway et al. | |
| 2009/0299393 A1 | 12/2009 | Martin et al. | |

FOREIGN PATENT DOCUMENTS

| | | |
|---|---|---|
| CA | 2389374 | 5/2001 |
| DE | 28 04 058 | 1/1978 |
| DE | 2821048 | 5/1978 |
| DE | 08435489 | 12/1984 |
| DE | 8435489 | 8/1986 |
| DE | 19703482 | 8/1998 |
| DE | 298 23 414 | 5/1999 |
| DE | 10010840 | 9/2001 |
| EP | 0201466 | 11/1986 |
| EP | 0737450 | 10/1996 |
| EP | 0 743 046 | 11/1996 |
| EP | 0 820 729 | 7/1997 |
| EP | 0 914 807 | 5/1999 |
| EP | 1005837 | 6/2000 |
| EP | 1351 626 | 7/2002 |
| EP | 0861634 | 8/2002 |
| EP | 0832606 | 6/2003 |
| EP | 0826342 | 10/2003 |
| EP | 0752236 | 12/2003 |
| EP | 1400219 | 3/2004 |
| EP | 0964659 | 9/2004 |
| EP | 1225844 | 7/2005 |
| EP | 1009296 | 11/2005 |
| EP | 1009295 | 12/2005 |
| EP | 1266639 | 8/2006 |
| EP | 1266640 | 8/2007 |
| FR | 2 343 488 | 3/1976 |
| GB | 2020557 | 5/1978 |
| GB | 1536019 | 12/1978 |
| JP | 02-255157 | 10/1990 |
| JP | 2001-178830 | 7/2001 |
| JP | 2003-010193 | 1/2003 |
| WO | WO 96/17634 | 6/1996 |
| WO | WO 96/28116 | 9/1996 |
| WO | WO 98/55175 | 12/1998 |
| WO | WO 99/16382 | 4/1999 |
| WO | WO 99/23976 | 5/1999 |
| WO | WO 99/25252 | 5/1999 |
| WO | WO 99/29264 | 6/1999 |
| WO | WO 99/44542 | 9/1999 |
| WO | WO 99/48400 | 9/1999 |
| WO | WO 99/48429 | 9/1999 |
| WO | WO 99/48440 | 9/1999 |
| WO | WO 00/12166 | 3/2000 |
| WO | WO 01/32099 | 5/2001 |
| WO | WO 01/45566 | 6/2001 |
| WO | WO 01/72240 | 10/2001 |
| WO | WO 02/054980 | 7/2002 |
| WO | WO 2004/008991 | 1/2004 |
| WO | WO 2007/092820 | 8/2007 |
| WO | WO 2008/131116 | 10/2008 |
| WO | WO 2009/034456 | 3/2009 |
| WO | WO 2009/086482 | 7/2009 |

OTHER PUBLICATIONS

Examiner's First Report for Australian Patent Application No. 2006-350952, dated May 11, 2010 in 3 pages.

Henkes et al., A Novel Microcatheter-Delivered, Highly-Flexible and Fully-Retrievable Stent, Specifically Designed for Intracranial Use, Interventional Neuroradiology, 2003, vol. 9, pp. 391-393.

International Preliminary Report on Patentability and Written Opinion of the International Searching Authority for PCT/US06/041695 mailed on May 28, 2008.

Canadian Office Action for Canadian Application No. 2,666,491, dated Dec. 10, 2010 in 3 pages.

Chinese Office Action for Chinese Application No. 200680056224.8, dated Nov. 11, 2010, in 15 pages.

Office Action for U.S. Appl. No. 11/924,369, dated Sep. 29, 2009, in 21 pages.

Second Office Action for U.S. Appl. No. 11/924,369, dated May 13, 2010, in 21 pages.

* cited by examiner

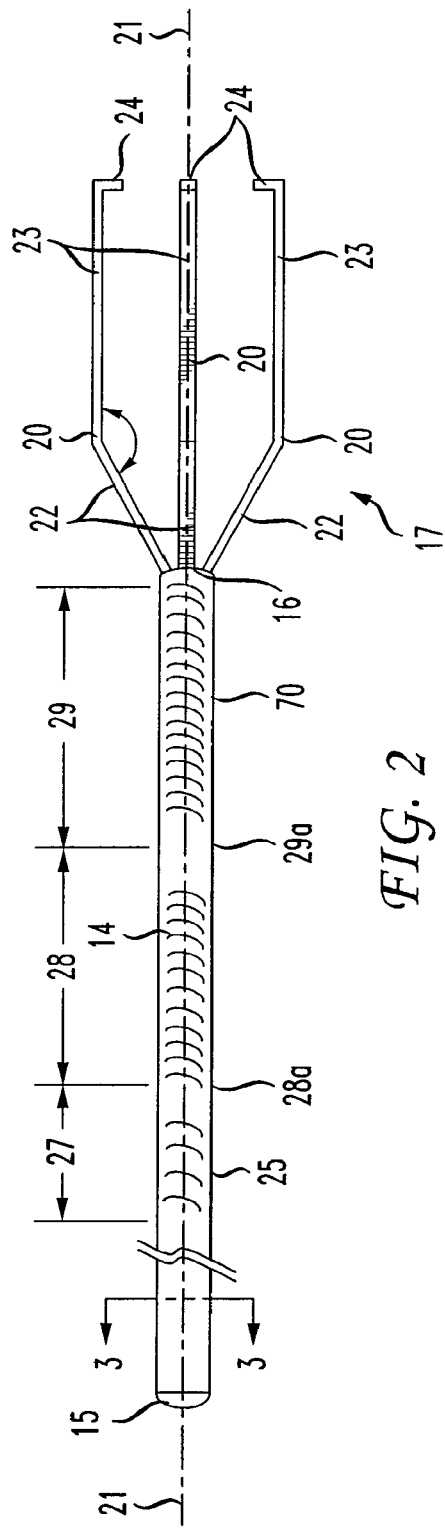
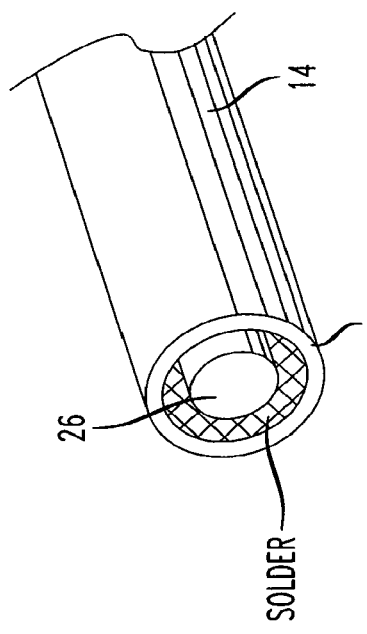
FIG. 2
FIG. 3

INTRACORPOREAL GRASPING DEVICE

CROSS REFERENCE TO RELATED APPLICATIONS

This application is a continuation from U.S. patent application Ser. No. 11/924,369, filed Oct. 25, 2007, which claims the benefit of priority under 35 U.S.C. §119(e) to U.S. Provisional Patent Application No. 60/854,439, filed Oct. 26, 2006, each of which is incorporated in its entirety by reference herein.

FIELD OF THE INVENTION

The invention pertains to an intracorporeal device and method for grasping objects within a patient's body and withdrawing the grasped objects from the patient's body. More specifically, the intracorporeal device is a grasping device having an internal shaft for removing an object, such as from a patient's vasculature.

BACKGROUND OF THE INVENTION

Developments in medical technology and associated treatments have been focused on clearing or removing thromboembolisms or "blood clots" from the cervical and cerebral vasculature in order to treat thromboembolic stroke victims. Thromboembolic stroke is a life threatening condition that consists of arrested blood flow to a region of the brain due to a thromboembolisum blocking a blood vessel feeding that region. Such thrombi often originate in the left heart chambers, break free into the aorta and flow downstream into the cervical neck arteries e.g. carotid arteries, and then ultimately lodge into a narrowed vessel somewhere down the narrowing vascular tree of the cerebral arteries associated with the brain in the head. Once lodged, the thrombus occludes flow along the vessel downstream of the blockage, thus arresting blood flow to the downstream blood vessel and causing the stroke.

Several grasping device assemblies and methods have been disclosed specifically for removing thrombi from the cervical and cerebral vessels in order to treat thromboembolic stroke. However, many of these devices have grasping assemblies that are not well adopted for delivery to distal regions of the cerebral vessels where many thromboembolisms are known to cause a debilitating stroke.

U.S. Pat. No. 6,679,893 describes a grasping device for removing thrombi from the cervical and cerebral vessels in order to treat thromboembolic stroke. This patent describes several grasping assemblies that may be utilized in its device. However, it is desired to have more flexibility in the selection of grasping assemblies depending on the type and location of the thrombi.

When retrieving a neurovascular clot or foreign body, a device having a distal grasping end with greater flexibility is desired. It is also desired to have a distal grasping end that is easily manufactured based on the desired flexibility.

BRIEF SUMMARY OF THE INVENTION

The invention pertains to an intracorporeal device and method for grasping objects within lumen of a human body and withdrawing the grasped objects from the human body.

In one aspect, an intracorporeal grasping device includes an elongated core having a proximal end portion and a distal end portion. The elongated core includes a tube having a variable flexibility along a length from the proximal end portion to the distal end portion. A grasping configuration is disposed to the distal end portion of the elongated core member for grasping an object from a human body.

In another aspect, an intracorporeal grasping device includes a movable elongated core having a proximal end and a distal end. The elongated core includes a plurality of flexion regions having different flexions along a length from the proximal end to the distal end portion. A grasping configuration is provided at the distal end of the elongated core for retaining and capturing objects.

In yet another aspect, an intracorporeal grasping device includes a tubular member for entering a lumen of a human body and the tube member having a distal end portion. An elongated core member is disposed with the interior cavity of the tubular member for rotational or slidably movement within the tubular member and the elongated core member having a proximal end portion and a distal end portion. A grasping configuration is provided for capturing an object (e.g., clot or debris) therein in which the grasping configuration is formed by at least one movable jaw attached to the distal end portion of the elongated core member and a length portion of the distal end portion of the tube member.

In another aspect, an intracorporeal grasping device includes a tubular member for entering a lumen of a human body and the tubular member having a distal end portion. An elongated core member is disposed with the tubular member and the elongated core member has a proximal end portion and a distal end portion. A grasping configuration captures an object in which the grasping configuration includes unitarily formed plurality of movable jaws attached to the distal end portion of the elongated core member.

In another aspect, an intracorporeal grasping device includes a tubular member for entering a lumen of a human body and the tubular member has a distal end portion. An elongated core member being disposed with the tubular member and the elongated core member has a proximal end portion and a distal end portion. The device includes a grasping configuration for capturing an object therein, in which the grasping configuration is formed by a plurality of loop members attached to the distal end portion of the elongated core member.

In one aspect, an intracorporeal grasping device includes a tubular member for entering a lumen of a human body and the tubular member having a distal end portion. An elongated core member being disposed with the tubular member and the elongated core member having a proximal end portion and a distal end portion. A grasping configuration is provided for capturing an object therein, in which the grasping configuration is formed by at least one spiral member having a distal tip for penetrating an object to be removed from a human body lumen. In the device has the spiral member provided at the distal end portion of the elongated core member.

An intracorporeal grasping device includes a tubular member for entering a lumen of a human body and the tubular member having a distal end portion. An elongated core member is disposed with the tubular member and the elongated core member has a proximal end portion and a distal end portion. A grasping configuration captures an object therein, in which the grasping configuration is formed by at least one web member for retaining an object to be removed from a human body lumen, the web member being provided at the distal end portion of the elongated core member.

In various other aspects, at least one of the jaws may include an engaging surface and an opposing surface, the engaging surface including a plurality of engaging elements provided along a longitudinal length thereof and the engaging elements. In another aspect, wherein the engaging elements are provided as ribs inwardly extending for capturing an object. In another aspect, at least one of the jaws is perforated at the location of the ribs.

In another aspect, at least one of the jaws has a distal end with an aperture and the jaw includes a lumen along a length enabling a fluid communications pathway to a distal end of the jaw.

The above and other aspects, features and advantages of the present invention will be readily apparent and fully understood from the following detailed description illustrative embodiments in conjunction with the accompanying drawings, which are included by way of example, and not by way of limitation with regard to the claimed invention.

BRIEF DESCRIPTION OF THE DRAWINGS

FIG. 2 is an elevational view of the grasping device shown in FIG. 1.

FIG. 3 is an enlarged section view of an elongated core member taken along the line 3-3 of FIG. 2.

FIG. 17A is an elevational view of the grasping device; FIG. 17B is a front axial view of the grasping device; and FIG. 17C is a sectional view taken along line 17C-17C in FIG. 17A.

DETAILED DESCRIPTION

The following embodiments and aspects thereof are described and illustrated in systems and methods which are meant to exemplary and illustrative and non-limiting in scope.

FIGS. 1-6 schematically illustrate an intracorporeal grasping system 10. In one embodiment by way of example, the grasping system 10 includes a grasping device 11, a delivery catheter 12 and a guide catheter 13. In some instances only the grasping device 11 and either the delivery catheter 12 or the guide catheter 13 are used, but not both.

Figure 1:
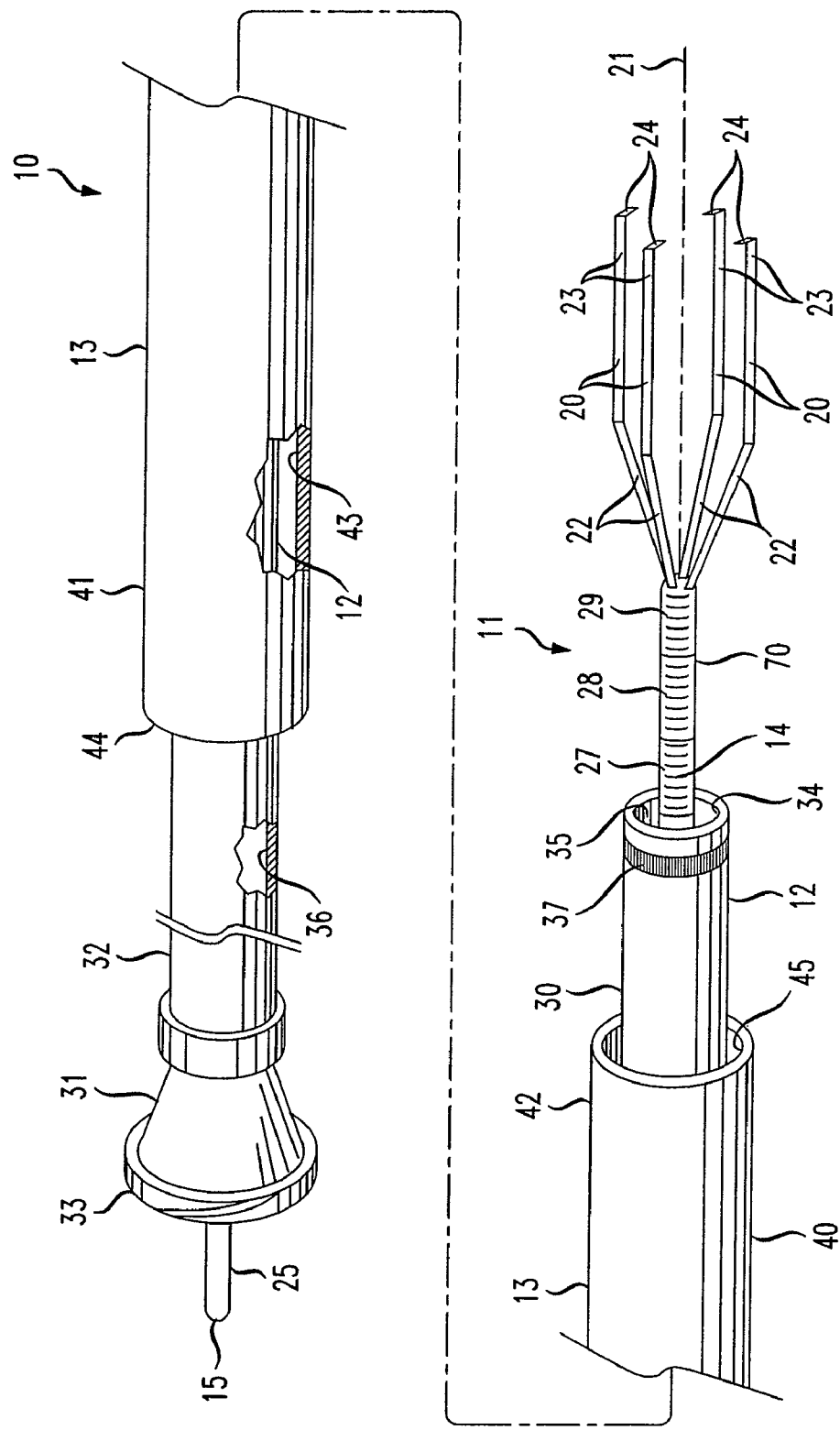
FIG. 1 is a perspective view of schematic representation of an intracorporeal grasping system according to the teaching of present invention.

As shown in FIG. 1 and in greater detail in FIG. 2, the grasping device 11 includes an elongated core member 14 having a proximal end 15 and a distal end 16. The grasping device 11 further includes a grasping configuration 17 attached to the distal end of the core member 14. The core member 14 can have a number of arrangements. In one embodiment by way of example, core member 14 is provided with variable bending flexibility along a predetermined length. Hence, this configuration of the core member 14 allows for improved transluminal manipulation of the grasping device 11 in a human body. In one construction, core member 14 is flexible in nature so as to traverse the potentially tortuous and/or angled geometry of the cervical vascular tree.

With reference to FIG. 3, elongated core member 14 includes a cylindrical tube 25 having a generally uniform diameter. A generally solid cylindrical core wire 26 is concentrically disposed within the cylindrical tube 25. A circumferential gap between the tube 25 and wire 26 may be filled with solder, for example. The solid cylindrical core wire prevents uniform cylindrical tube 25 from excessive longitudinal elongating along its length.

In one embodiment by way of example, the flexibility of the uniform cylindrical tube 25 can be provided by a plurality of spaced circumferential slots 70 extending through the wall thickness (See FIG. 2). For ease of explanation, the term "density" with reference to cuts or slots of the core member, generally refers to the number of slots or cuts per a unit of length or area. Non limiting examples of a unit of length are a centimeter, an inch or smaller linear units. Likewise, a unit of area may be square inches or square centimeters and the like.

In accordance with an embodiment of the grasping device, the amount or magnitude of flexibility is proportional to the number of slots per unit of measure. For example, a high density of slots provides higher flexibility, than a lower density of slots. By changing the density and/or pattern of the circumferential slots, the flexibility of the elongated core member 14 can be changed.

Core member 14 may have a multi-flexion configuration that has separate regions of different flexions that each correspond to the flexibility, or lack thereof, for improved transluminal manipulation. This multi-flexion regional configuration provides adaptability for a practitioner to reduce steps for accessing or grasping an object or customize the access in body lumens to increase patient comfort. In one exemplary construction, the core member 14 may have three flex regions to accommodate to transluminal access. A first flexion region 29 may extend from the distal end 16 to a first intermediate position 29a along the length of the elongated core member 14. The first flexion region 29 is substantially flexible for improved comfort, for example. An adjacent second flexion region 28 may extend to another intermediate position 28a away from first intermediate position 29a along the length of the elongated core member 14. The second flexion region 28 may be less flexible than a first flex region 29 so as to allow the elongated core member 14 to traverse the vascular geometry in an improved fashion. A third flex region 27 may be provided adjacent to the second flexion region 28. The third flexion region 27 may be less flexible than the second flexion region and the first flexion region.

Referencing FIG. 2, in one construction, the uniform diameter tube 25 has a distal section 29, middle section 28 and proximal section 27 generally corresponding to the multi-flexion configuration in which each section has a different flexibility with respect to each other. For example, the distal section 29 may have a high flexibility, the middle section 28 may have a medium flexibility, and the proximal section 27 has a low or minimal flexibility. Hence, distal section 29 has the greatest flexibility of the sections 28, 27. These sections are all part of the same uniform cylindrical tube 25 having three distinct stiffness or flexion sections. In one embodiment, the distal section 29 of the core member 14 can be at least in part 10%-25% more flexible than the proximal section 27 of the core member 14. The middle section 28 can be at least in part 5%-20% more flexible than the proximal section 27. The distal section 29 can be 5%-20% more flexible than the middle section 28. In alternative embodiment, the distal section 29 of the core member can be at least in part 35%-50% more flexible than the proximal section 27 of the core member. The middle section 28 can be at least in part 30%-45% more flexible than the proximal section 27. The distal section 29 can be 30%-45% more flexible than the middle section 28. Nevertheless, other flexibility relative values are possible.

Any suitable number of stiffness/flexible sections could be used on the core member 14. In a specific non-limiting example, the dimensions of the first flexion region may be 3.0 cm from the distal end; second flexion region may have a length of 5.0 to 15.0 cm; and the third flexion region may have a length of 20.0 to 40.0 cm. Nevertheless, the length of the regions may be configured as desired by the practitioner. In an alternative embodiment, the density of the slots can be increased uniformly for a continuous transition from proximal low flexibility to distal high flexibility for the core member 14.

The solid cylindrical core wire 26 spans the length of the uniform cylindrical tube 25 and is affixed to the tube by any suitable method by soldering e.g. with silver or gold solder, brazing, welding, adhesives, mechanical connections or other suitable techniques. The solid cylindrical core wire 26 is preferably attached to the tube at least at both ends of the core wire.

The circumferential slots or cuts can be made by any suitable manufacturing technique, such as, for example, computer numerically controlled (CNC) microsawing, EDM wire cutting, or laser cutting.

The uniform cylindrical tube 25 is generally formed of a high strength material such as stainless steel, superelastic nickel-titanium alloy, cobalt-chromium-molybdenum alloys such as MP35N and Elgiloy or other material having suitable strength, stiffness, and other attributes for allowing percutaneous transluminal manipulation of the grasping device 11 as described herein. Suitable materials include but are not limited to 304SS or NITINOL.

As used herein, the term "superelastic shape memory material" refers to a class of metal alloys that have a stress-induced phase change from austenite to martensite and upon stress release, the material springs back to this original phase and shape. The material structure of a superelastic shape memory material regarding austenite and martensite is well-known to one of ordinary skill in the metallurgy art. A NiTi material or NiTi alloy may be used as an alloy material for the flex control member 21. As used herein, a NiTi superelastic shape memory material refers to an alloy that is an intermetallic compound of nickel and titanium having nearly equal mixtures as measured by weight. One composition of a NiTi superelastic shape memory material generally has a greater percentage of nickel by weight than titanium, such as 51%-56% of nickel, and preferably 54-55% nickel. The specific percentages of nickel and titanium can be adjusted by one of ordinary skill in the art. It should be recognized that additional metals, such as copper, iron, chromium, and cobalt, can be added to fine tune various properties of a NiTi superelastic shape set material.

One embodiment, core member 14 is preferably constructed from a superelastic shape set material commonly called NITINOL® depending upon the alloy composition. NITINOL® is a brand name which refers to Nickel Titanium Naval Ordinance Laboratory, a commercially available family of nickel titanium alloys. Among the suppliers, NITINOL® material can be obtained from NDC of Fremont, Calif. Nevertheless, there are numerous other suppliers of NiTi materials and NiTi superelastic shape set materials.

Figure 4:
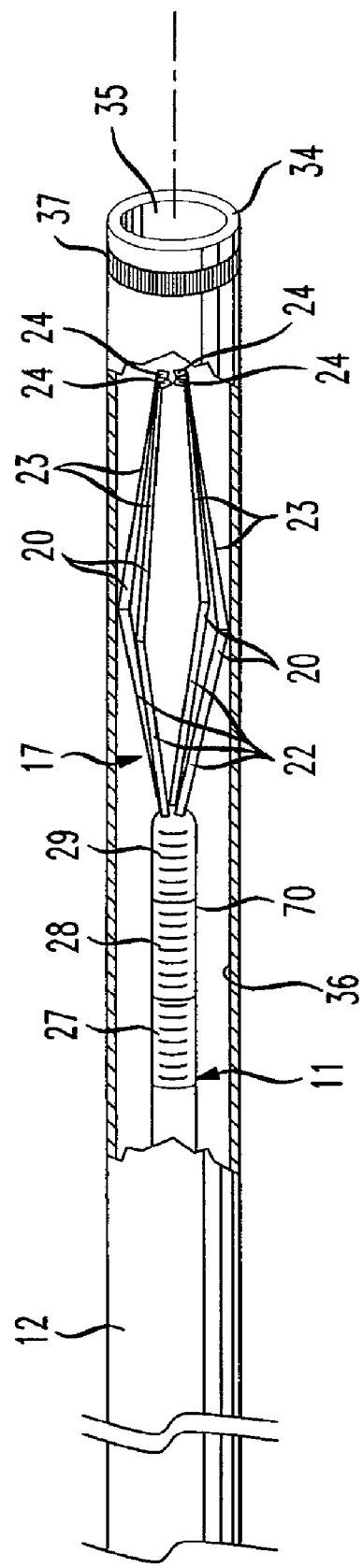
FIG. 4 shows a side elevational view, partially in section, of the grasping device shown in FIG. 2 in a closed configuration within the inner lumen of the delivery catheter.

The outer diameter of cylindrical tube 25 should be selected for slidable advancement within the inner lumen 36 of the delivery catheter (See FIGS. 1 and 4). Generally, outer diameter of cylindrical tube 25 is about 0.015 inch to about 0.040 inch, and preferably about 0.010 to about 0.038 inch. An outer lubricous coating (not shown) may be provided on the exterior of the cylindrical tube 25 at least along distal portion 27. Suitable coatings include fluoropolymers such as polytetrafluoroethylene (TEFLON) or hydrophilic materials.

The inner diameter of cylindrical tube 25 is provided in suitable diameter to enclose solid cylindrical core wire 26 therein. Generally, inner diameter of cylindrical tube 25 is about 0.005 inch to about 0.036 inch. A typical dimension of uniform cylindrical tube 25 is 0.016"OD×0.009"ID. Nevertheless, other dimensions may be used.

The grasping assembly 17 may be any suitable grasping assembly. As depicted in FIGS. 1 and 2, the grasping assembly 17 has a plurality of arms 20 disposed about the longitudinal axis 21 of the device 11 with proximal arm sections 22 secured to the distal end 16 of the core member 14 and distal arm sections 23 which extend essentially parallel to the longitudinal axis 21 e.g. not more than 5° from a line parallel to longitudinal axis when the grasping assembly 17 is in an expanded configuration as shown. The distal arm sections 23 have inwardly extending, object engaging elements 24 at their distal ends. The bluntness of the object engaging element 17 provides a non-traumatic feature to the distal end of the arms 20. The proximal portion 25 of the grasping device 11 is usually of uniform outer diameter and is of sufficient length so that the proximal end 15 extends out of the delivery catheter 12 when the grasping assembly 17 extends out the distal end of the delivery catheter.

As shown in FIG. 1 the delivery catheter 12 has a tubular body 30 with an adapter 31 on the proximal end 32, a port 33 in the adapter 31, a distal end 34, a port 35 in the distal end and an inner lumen 36 extending between and in fluid communication with proximal port 33 in the adapter 31 and the distal port 35. A radiopaque marker 37 is provided on the distal end 34 to facilitate fluoroscopic observation of the distal end of the delivery catheter 12 during a procedure within a patient's body, such as a thrombectomy. The inner lumen 36 is configured to slidably receive the grasping device 11 with the grasping assembly 17 in the contracted configuration as shown in FIG. 4. The adapter 31 is preferably provided with a hemostatic valve (not shown).

Delivery catheter 12 is generally constructed to track over a conventional guidewire beyond the guide catheter 13 in the cervical anatomy and into the cerebral vessels associated with the brain and may also be chosen according to several standard, "microcatheter" designs that are generally available. Accordingly, delivery catheter 12 has a length that is at least 125 cm long, and more particularly may be between about 125 cm and about 175 cm long. Typically, the delivery catheter 12 is about 155 cm long. The inner lumen 36 of the delivery catheter generally has an inner diameter between about 0.01 inch and about 0.08 inch (0.25-2.03 mm). Commercially available microcatheters are generally suitable for use as delivery catheters.

Also shown in FIG. 1 is guide catheter 13 has a tubular body 40, a proximal end 41, a distal end 42, and an inner lumen 43 extending between a proximal port 44 in the proximal end and a distal port 45 in the distal end of the guide catheter. The proximal end 41 of guide catheter 13 may be provided with an adapter (not shown) having a hemostatic valve. Guide catheter 13 is generally constructed to bridge between a femoral artery access site and a cervical region of the carotid or vertebral artery and may be chosen according to several standard designs that are generally available. Accordingly, guide catheter 13 is generally at least 85 cm long, and more particularly may be between about 95 cm and about 105 cm long. Further to conventional and available designs, the inner lumen 43 of guide catheter 13 generally has an inner diameter that is between about 0.038 inch and 0.090 inch (0.88-2.29 mm), and more particularly may be between about 0.052 inch and about 0.065 inch (1.32-1.65 mm).

Grasping device 11 is configured to slidably fit within the inner lumen 36 of delivery catheter 12. For procedures involving distal locations of thromboembolic neurovascular occlusions, the grasping device 11 is configured to be delivered through the inner lumen 36 of the delivery catheter 12 with a diameter that is equal to or less than about 0.042 inches (1.07 mm), preferably less than about 0.022 inches (0.559 mm). In the case of use in a more distal, tortuous, and smaller vessel anatomy, configuration for delivery through a delivery catheter inner lumen less than 0.018 inch (0.457 mm) diameter may be used. For most neurovascular occlusions, the grasping device 11 is about 135 cm to about 300 cm long, and more particularly may be about 150 cm to about 200 cm long. Generally, the grasping device 11 is about 175 cm long and is adapted to be used in a delivery catheter 12 that is about 150 cm long. Nevertheless, other values for diameters and lengths are possible.

The device as described does not include a tapered core mandrel as disclosed in U.S. Pat. No. 6,679,893. Instead, the grasping elements are attached to the distal end of a generally uniform cylindrical tube in one embodiment.

Figure 5:
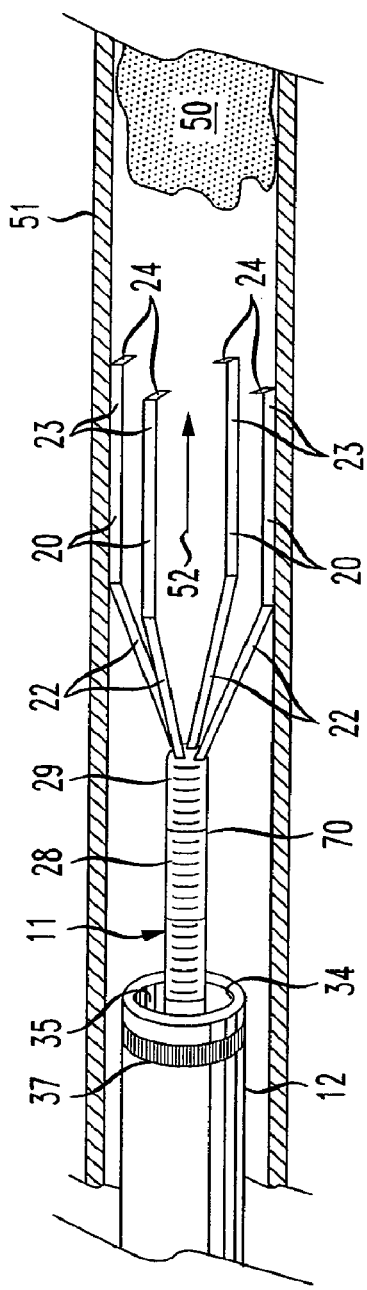
FIG. 5 depicts the grasping device disposed within the delivery catheter with the grasping assembly of the device extending out the port in the distal end of a delivery catheter into a body lumen adjacent to a thrombus and being in an expanded configuration therein.
Figure 7:
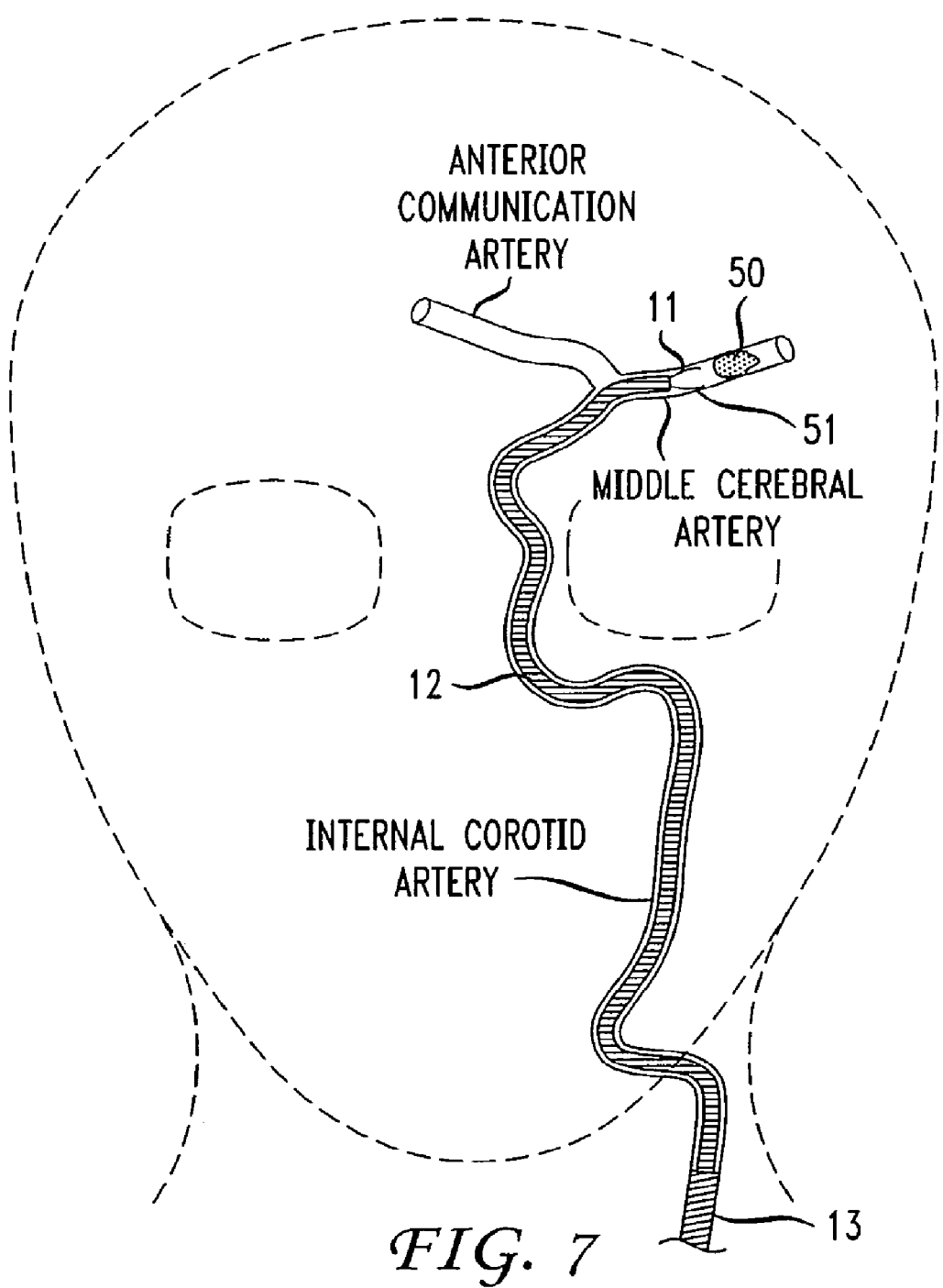
FIG. 7 is a schematic illustration of the grasping system shown in FIG. 1 operatively disposed in a left side internal carotid artery location in position to perform an exemplary thrombectomy procedure within the middle cerebral artery.

Grasping assembly 17 is adjustable between different configurations, namely, a completely contracted configuration or nearly contracted configuration as generally shown in FIG. 4 to facilitate disposition within the inner lumen 36 of delivery catheter 12. In another arrangement grasping assembly has a completely expanded configuration or nearly expanded configuration as generally shown in FIGS. 1, 2 and 5 to facilitate advancement of the expanded grasping assembly 17 within the body lumen about the object to be captured. In yet another arrangement, assembly 17 has a partially contracted configuration to hold onto or capture the object as generally shown in FIG. 7. Grasping assembly 17 is shown in FIGS. 1, 2 and 5 in the expanded configuration which is generally defined by each of the arms 20 in a completely expanded position and the distal arm sections 23 being generally parallel or nearly parallel to longitudinal axis 21, which in a preferred embodiment is the relaxed memory state for the arms 20.

Figure 6:
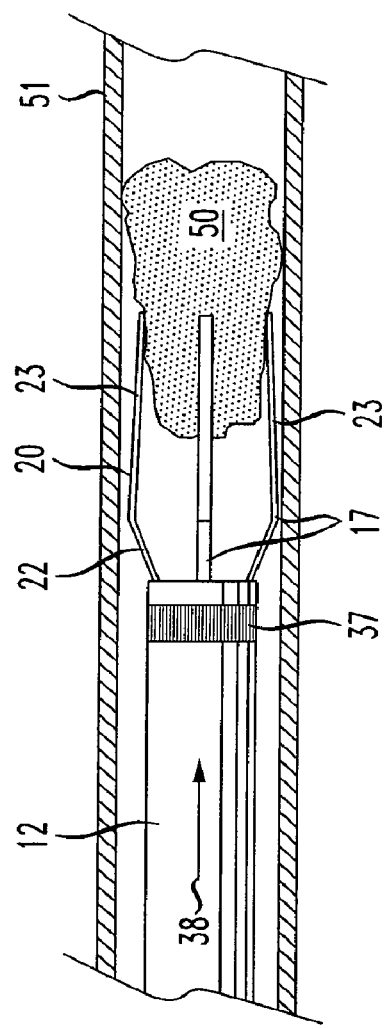
FIG. 6 illustrates an elevational view of the grasping device within a delivery catheter having the grasping assembly on the distal end of the device being in a partially contracted configuration about a thromboembolism.

Grasping assembly 17 is adjustable from the expanded configuration as generally shown in FIG. 5 to the contracted or partially contracted configuration by the application of force against the inclined proximal arm sections 22 by advancing the distal end 35 of the delivery catheter 12 as shown by the arrow 38 in FIG. 6 against the inclined proximal arm sections.

Arms 20 may be constructed of various materials having suitable strength, elasticity and memory for use in engaging and removing an object such as thrombus from a body lumen, particularly a cerebral vessel. However, arms 20 are generally constructed from a metal which may be for example platinum (or alloys thereof), stainless steel, superelastic shape memory material, or high strength cobalt-chromium-molybdenum alloys. Platinum or alloys thereof are preferred because they provide a particular beneficial combination of a non-traumatic distal tip for the arms 20 and radiopacity for fluoroscopic observation of the arms in an intracorporeal procedure.

There are any number of alternative arrangement for practicing techniques and aspects of the grasping device 11. More specific features of the use of the device and system in capturing and removing, for example, thromboembolic occlusions from the distal cerebral vessels are described in the foregoing. Nevertheless, the inventive aspects of the grasping device 11 can be used for any number of alternative arrangements. Hence, the following example is illustrative of a method of using the grasping device 11.

First, an access site is prepared as either a puncture wound (i.e. Seldinger technique) or as a surgical cut-down, typically in the femoral artery although in rare circumstances vascular access may be made at other peripheral vessels such as a brachial artery. An introducer (not shown) may be used to provide hemostatic access at the access site via an incorporated hemostatic valve. Guide catheter 13 is then advanced through the introducer until distal end 42 is positioned with distal port 45 at a region of a cervical vessel 50, thereby providing transluminal access to the cervical vascular tree as shown in FIG. 7. Delivery catheter 12 is advanced through the inner lumen 43 of guide catheter 13 and out the distal port 45 thereof until the distal end 34 of the delivery catheter is positioned adjacent to the thromboembolism 50 located in the middle cerebral artery 51.

In the case where the distal location of the thromboembolism is beyond a bifurcated vessel or otherwise tortuous cerebral vessels, the delivery catheter 12 may be advanced over a conventional guide wire (not shown). Once the delivery catheter 12 is positioned adjacent to the thromboembolism 50, the guide wire is removed from the patient and is then replaced with grasping device 11. Grasping device 11 is advanced through the inner lumen 36 of the delivery catheter in the contracted configuration as shown in FIG. 5, until it exits through distal port 35 into the blood vessel 51 where the grasping assembly 17 self-adjusts to the expanded configuration with arms 20 in a radially expanded position. Grasping assembly 17 is then advanced, as indicated by the arrow 52, in the expanded configuration distally so that arms 20 advance around the thromboembolism 50 as shown in FIG. 5. Then, delivery catheter 12 is advanced distally to press against proximal arm sections 22 to force distal arm sections 23 to rotate radially inwardly to a partially contracted configuration so that the object engaging members 24 engage the thromboembolism 50 as shown in FIG. 7. Thereafter, the grasping device 11, delivery catheter 12, and thromboembolism 50 may be removed from the location and further from the body, either through guide catheter 13 or together in combination with guide catheter.

Figure 8A:
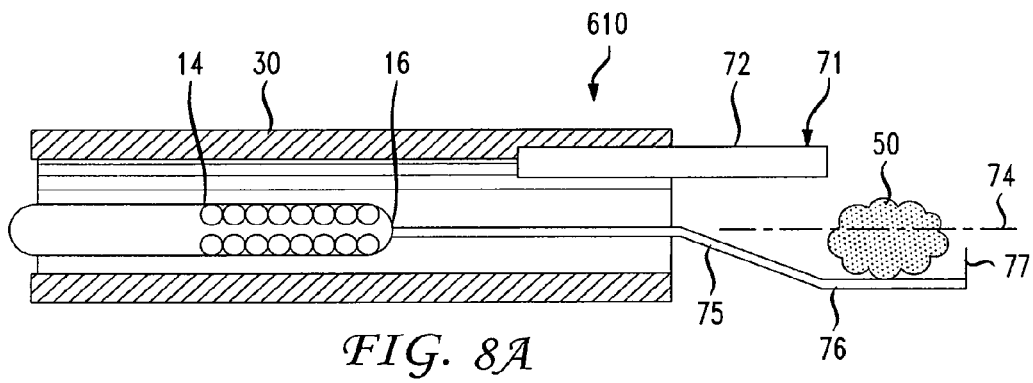
FIGS. 8A-8C illustrate an alternative embodiment of a grasping system according to the teaching of the present invention.
Figure 8B:
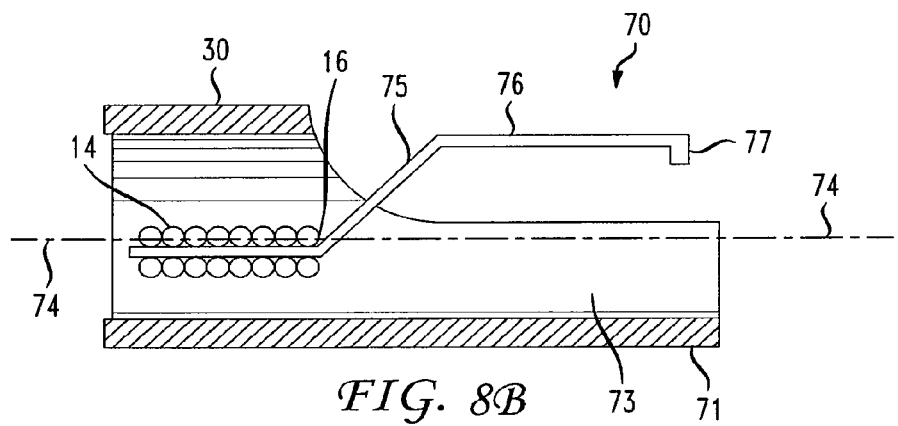
Figure 8C:
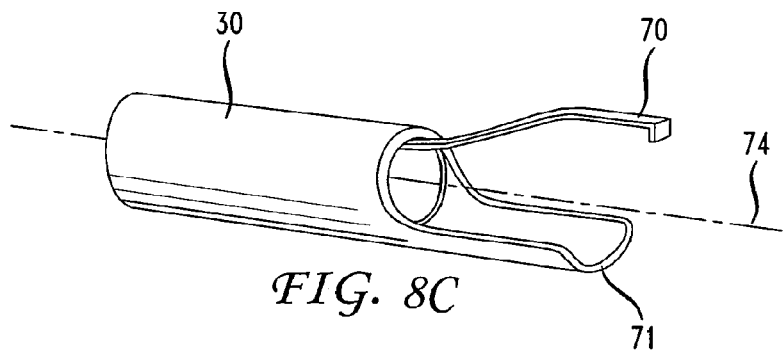

FIGS. 8A-8C schematically illustrate an alternative intracorporeal grasping system 610. Intracorporeal grasping system 610 includes at least one jaw 70 and a scoop 71 used to extract the object to be captured between the jaw 70 and scoop 71. The scoop may be a rigid member 72 that extends from tube 30 as shown in FIG. 8A, or a catheter scoop 73 formed by cutting away the tip of tube 30 to form a scoop as shown in FIG. 8B and FIG. 8C. A single jaw is depicted in these figures; however, more than one jaw may be used. The cutting operation to form the scoop 73 can be a suitable method such as laser cutting.

The jaw 70 is generally disposed along the longitudinal axis 74 and has a proximal arm section 75 secured to the distal end 16 of the elongate core member 14. The proximal arm section 75 is inclined from the distal end 16 of the elongate core member 14. The inclined proximal arm section 75 functions to aid in placing the jaw 70 of the grasping assembly 17 into a contracted or partially contracted configuration about the longitudinal axis 74 by the force applied to the inclined section by advancement of the distal end of the delivery catheter 12 and has a length selected to provide the desired radial spacing between the distal arm section 76 and the scoop 71. An inwardly extending object engaging element 77 is disposed at the distal end of jaw 70. The jaw 70 typically extends beyond the length of the scoop as shown in FIG. 8A.

In one operation, the scoop 71 is forced, wedged, or placed under the object to be captured. The jaw 70 extends beyond the length of the scoop and is retracted by moving the elongate core member 14 inward distally. As the jaw 70 is being retracted, it is forced to bite down on the object towards the longitudinal axis 74. When jaw 70 engages the object it then pulls the object along the length of the scoop 71 into tubular body 30 for removal.

Jaw 70 may be constructed from a flat ribbon or wire. Jaw 70 may be constructed of various materials having suitable strength, elasticity and memory for use in engaging and removing an object such as thrombus from a body lumen, particularly a cerebral vessel. In one embodiment, jaw 70 may be generally constructed from a metal which may be for example platinum (or alloys thereof), stainless steel, super-elastic nickel-titanium alloy, or high strength cobalt-chromium-molybdenum alloys.

Rigid member 72 may be constructed of various materials having suitable strength and is generally constructed from a metal which may be for example platinum (or alloys thereof), stainless steel, super-elastic nickel-titanium alloy, or high strength cobalt-chromium-molybdenum alloys.

Figure 9A:
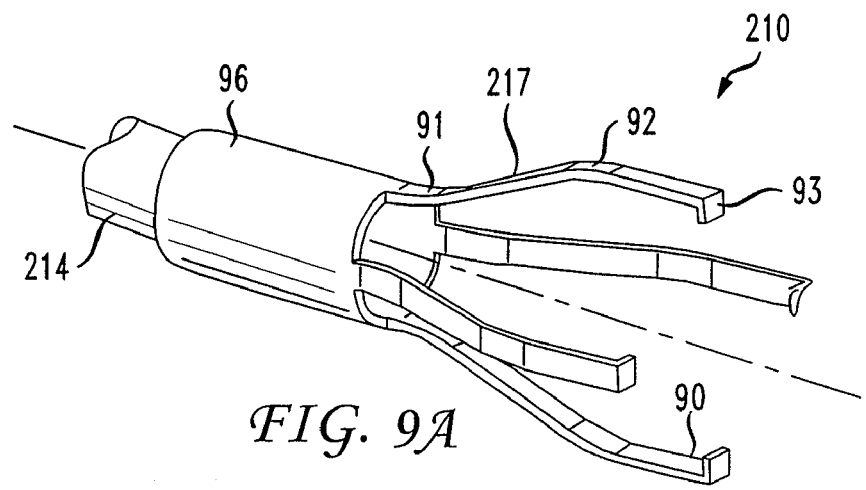
FIGS. 9A-9C illustrate an alternative embodiment of a grasping system according to the teaching of the present invention.
Figure 9B:
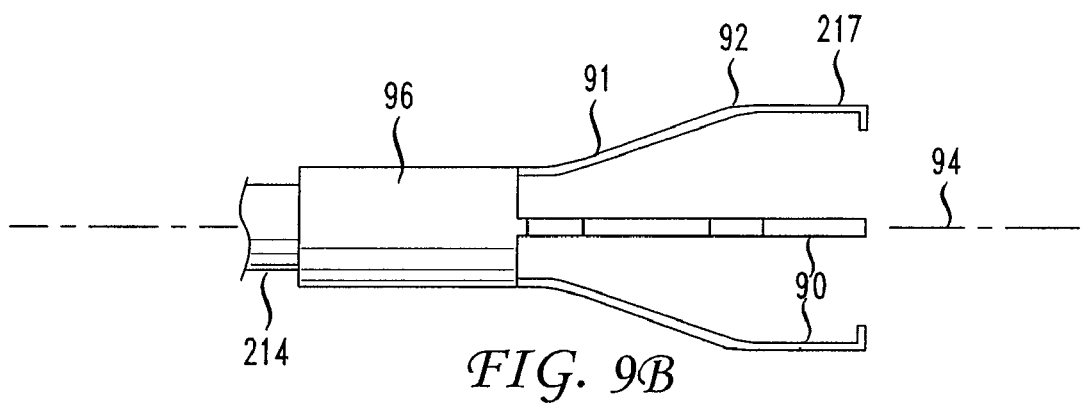
Figure 9C:
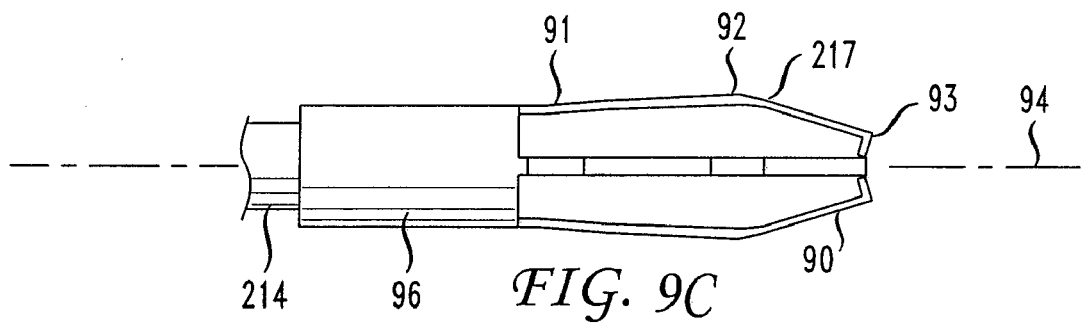

FIGS. 9A-9C schematically illustrate an alternative intracorporeal grasping system 210. A grasping configuration 217 is provided for capturing an object (e.g., clot or debris) therein, in which the grasping configuration comprises unitarily formed plurality of movable jaws 90 attached to the distal end portion of the elongated core member 214. It is noted that core member 214 can have the construction of core member 14 as well as other constructions.

In another embodiment, jaws 90 are formed from thin tubing 96 which is cut, e.g. with a laser, to form narrow jaws 90. (See FIG. 9A). Each jaw 90 has a proximal arm section 91 extending from tubing 96. As shown in FIG. 9B, the proximal arm section 91 is inclined from the tubing 96. The inclined proximal arm section 92 functions to aid in placing the jaws 90 of the grasping configuration 217 into a contracted or partially contracted configuration about the longitudinal axis 94 by the force applied to the inclined section by advancement of the distal end of the delivery catheter 12 (FIGS. 1-2) and has a length selected to provide the desired radial spacing between the distal arm sections 92. Inwardly extending object engaging elements 93 are disposed at the distal end of jaws 90.

Tube 96 is disposed onto the distal end of the elongate core member 214, as shown in FIG. 9B and adhered into place or fastened or otherwise attached thereto. In operation, the jaws 90 extend along a length of the object to be removed and are retracted by retracting elongate core member 14. As the jaws are being retracted, they are forced to bite down on the object and then pull the object into tubular body 30.

As with various jaws disclosed herein, jaws 90 may be constructed of various materials having suitable strength, elasticity and memory for use in engaging and removing an object such as thrombus from a body lumen, particularly a cerebral vessel. However, jaws 90 are generally constructed from a metal which may be for example platinum (or alloys thereof), stainless steel, super-elastic nickel-titanium alloy, or high strength cobalt-chromium-molybdenum alloys.

It is noted that jaw assemblies generally have an inwardly extending object engaging elements disposed at the distal end of jaws. This is shown in the embodiments of FIGS. 8-9 above, for example. In further embodiments, the jaws may contain engaging elements. The jaws may be suitable jaws as any embodiments described herein. FIGS. 10A-10F illustrates alternative arrangement of jaws with various engaging elements for removing a thrombus, for example.

Figure 10A:
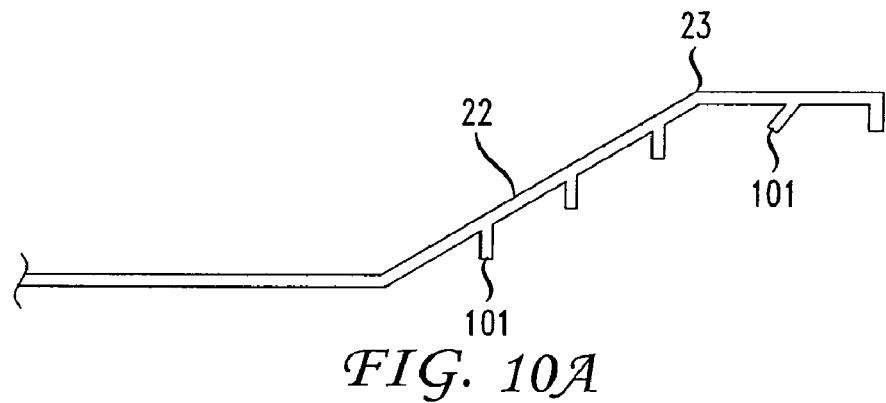
FIGS. 10A-10F illustrate an alternative embodiments of grasping device components according to the teaching of the present invention.
Figure 10B:
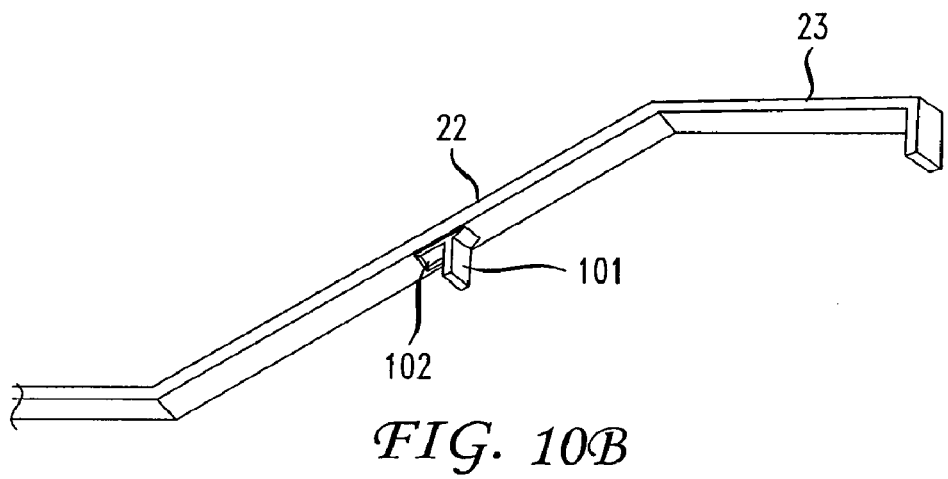
Figure 10C:
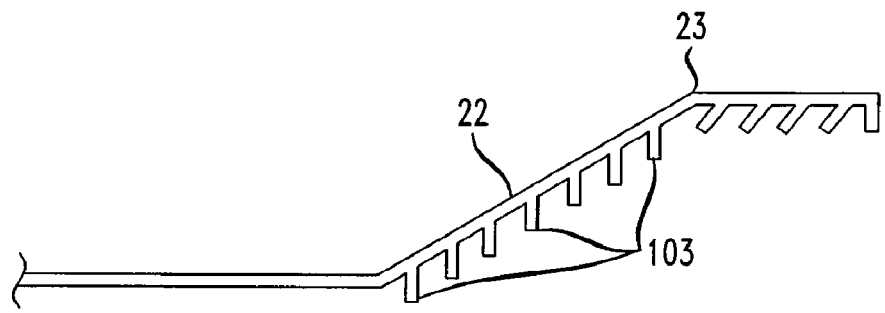

Engaging elements allow the jaw to grip the object to be removed. In addition to engaging elements 24 in FIG. 10A, a plurality of engaging elements can be applied to arm segment 22 and/or arm segment 23 (e.g., FIGS. 1-4). The engaging elements 101 extend towards the object to be removed and may be applied as a separate member for the arm segments, such as by soldering as shown in FIG. 10A. Alternatively, the engaging elements may be formed by cutting tabs 102 in the arm segments and bending inward as shown in FIG. 10B, or by pressing grooves or ribs 103 onto the inside surface of the ribbon forming a jaw as shown in FIG. 10C.

Figure 10D:
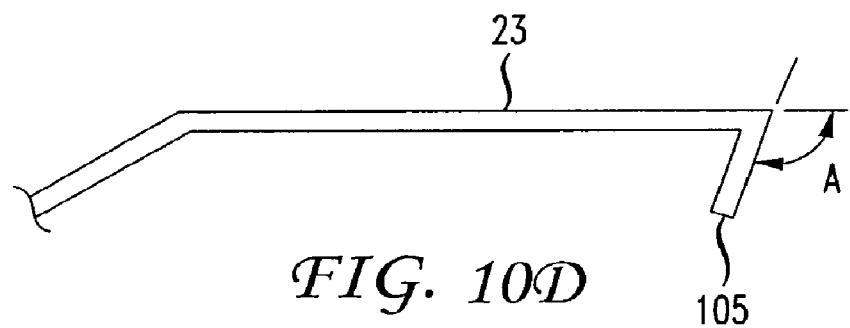
Figure 10E:
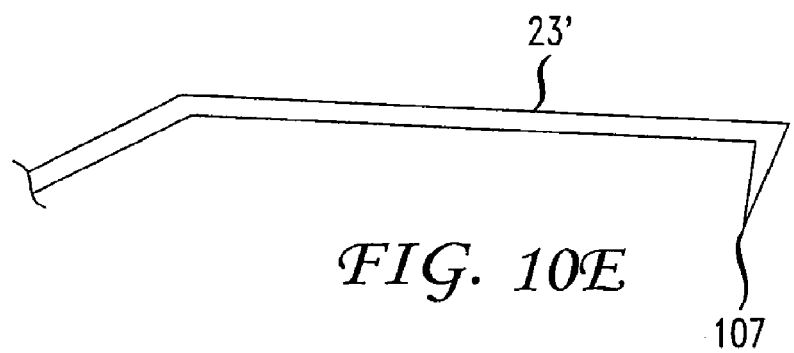
Figure 10F:
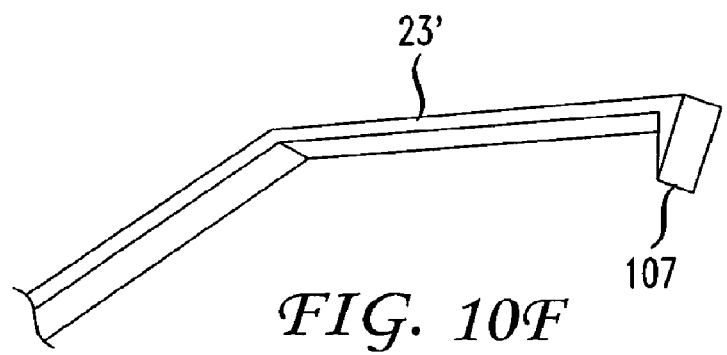

In one arrangement, the arm segment 23 with engaging elements may include a distal blunt edge 105 as shown in FIG. 10D or arm segment 23' with a distal sharp edge or distal "bladed" edge 107 as shown in FIGS. 10E-F. A distal blunt edge 105 is useful for grabbing the debris and pulling into the tubular member 30. As shown in FIG. 10D, the distal portion can be angled inward more than 90 degrees from the horizontal as denoted by angle "A". For example, the angle may be 91-97 degrees or 93-95 degrees. Additionally, the distal sharp edge 107 is useful for grabbing the debris and pulling into the tubular member 13, but also useful for cutting or biting off chunks of the debris (clot), for example, if the debris is too large to remove in as a single unit.

Figure 11:
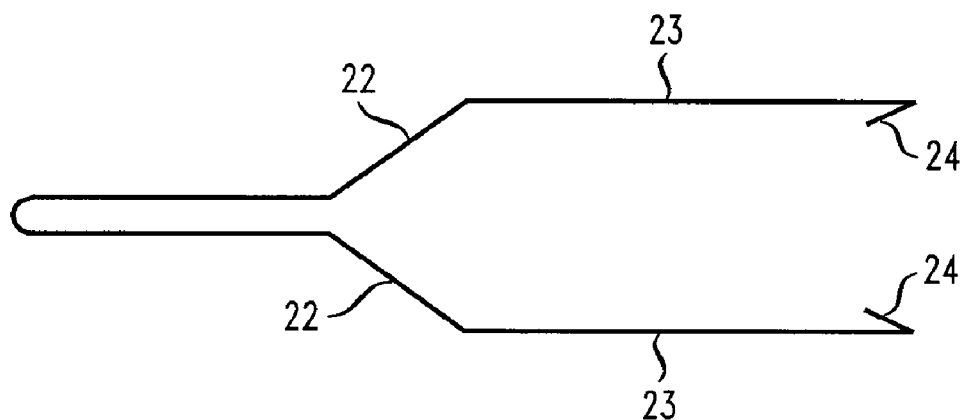
FIG. 11 illustrates an alternative embodiment of a grasping device component according to the teaching of the present invention.
Figure 12A:
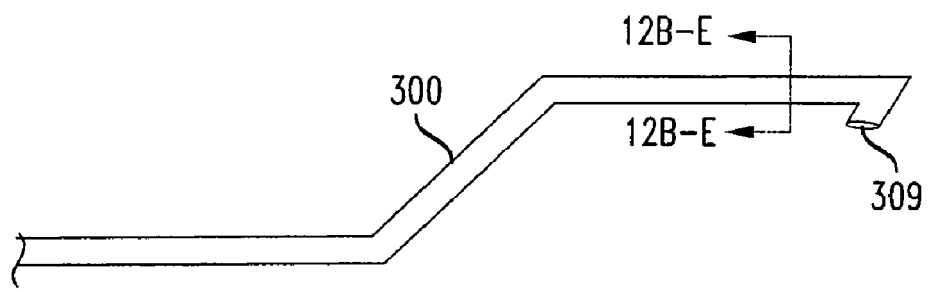
FIGS. 12A-12E illustrate alternative embodiments of grasping device components according to the teaching of the present invention.
Figure 12B:
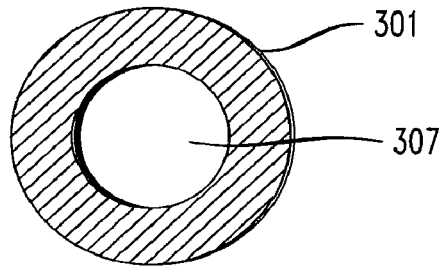
Figure 12C:
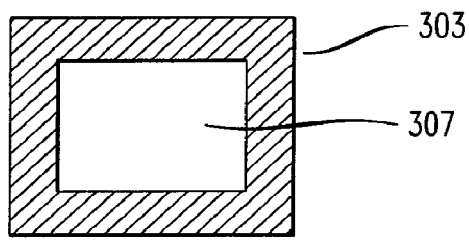
Figure 12D:
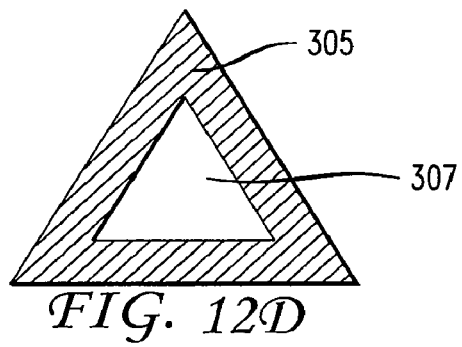
Figure 12E:
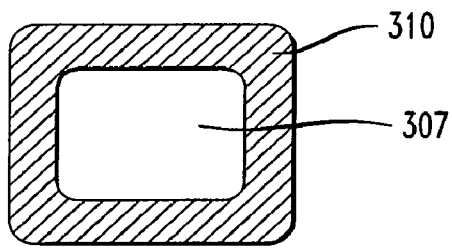

As shown in FIG. 11, jaws can be formed of a unitary piece of ribbon or wire, such as platinum ribbon or wire, which is bent into a U or V shape. Nevertheless, other shapes are possible. The two edges of the ribbon or wire form two jaws which include two arm segments 22, 23 and two engaging elements 24. The ribbon or wire is attached to elongate core member 14 such as via coil 19.

FIGS. 12A-12E schematically illustrate an alternative embodiment for a grasping assembly component. As shown in FIGS. 12A-12E, the jaws 300 may be formed from tubing having a desired cross-section, such as a circular 301, rectangular 303, triangular 305, oval 310 or other shape to provide benefits of grasping objects in a human body or surgical benefits. The hollow interior of the tube forms a lumen 307 which can be used to inject or deliver fluidic substances or medicament to the object to be removed at the distal end 309. In one embodiment, the distal end 309 of the jaws 300 has an aperture for delivering fluids. In one example, a substance might be injected though the jaws 300 in order to soften the object to be removed. Nevertheless, different type of substances can be provided. Alternatively, a vacuum may be applied to the tube to remove fluids or to provide a negative pressure region at the distal end 309 of the jaws 300 to remove portions of the object designated for removal or other debris.

FIGS. 13A-13E illustrate an alternative intracorporeal grasping system 400. At least one jaw member collectively defines a loop configuration 405 to advantageously increase the coverage/grasping area of the objects to be grabbed and removed from the human body. Further, the loops retains the object specifically between the contact other loops. Hence, the grasping element 17 can be formed from a plurality of loops 405 (such as two loops) which engaged each to capture or clamp objects therein.

Figure 13A:
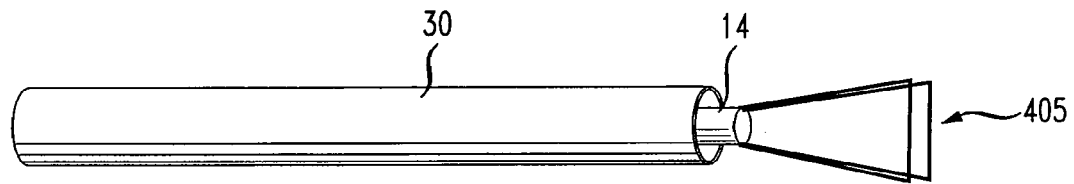
FIGS. 13A-13F illustrate another embodiment of a grasping system according to the teaching of the present invention.
Figure 13B:
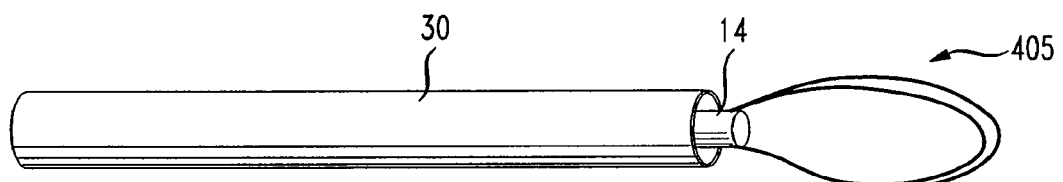

While the loop configuration is preferably a circle, it could be in the form of a myriad of different closed loops including without limitation ovals, squares and irregular shapes. Nevertheless, other shapes can be used. The loop should simply define a substantially closed configuration to retain the object therein. The loops can be of different shapes and forms and various cross-sections as is suitable for the particular type and shape of object to be removed. For example the loops may have a spatula shape as shown in FIG. 13A or a spoon shape as shown in FIG. 13B.

Figure 13C:
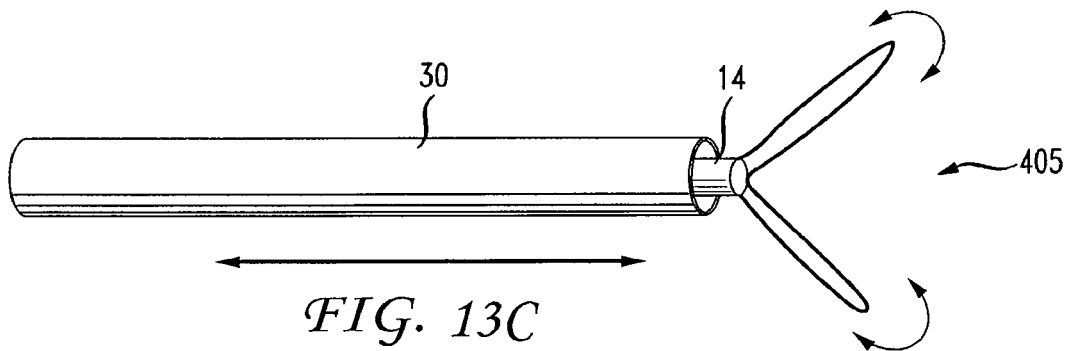
Figure 13D:
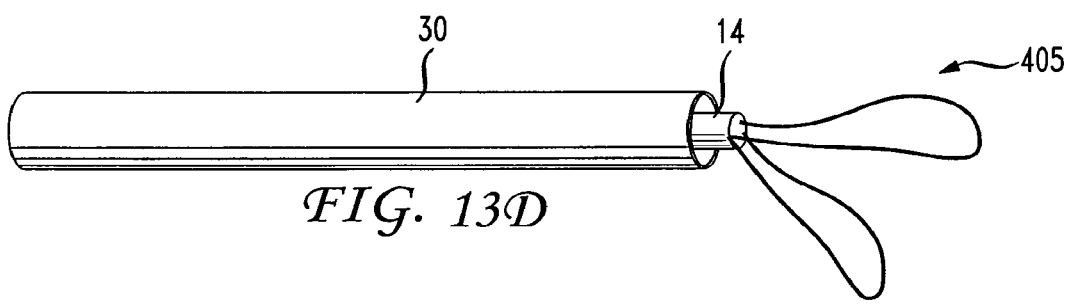
Figure 13F:
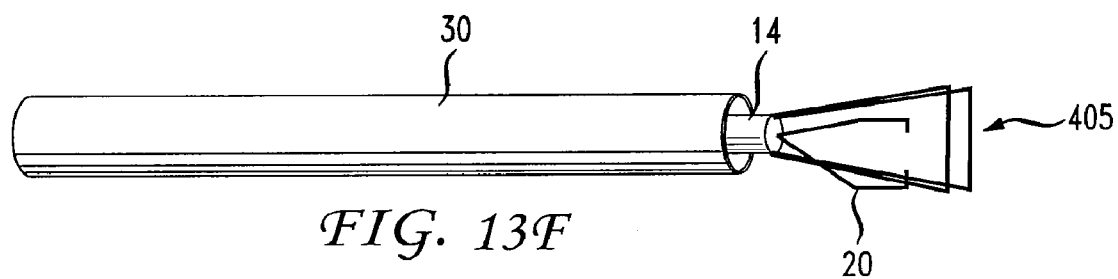
Figure 13E:
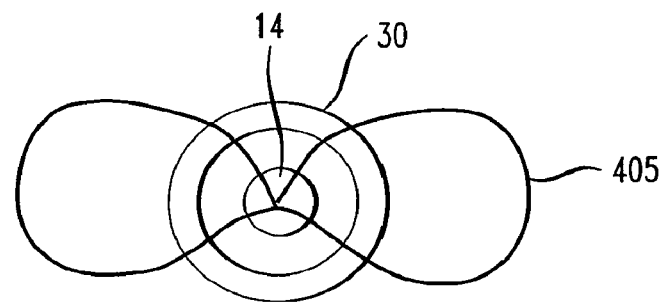

The loops are attached to the elongate core member 14 such as a core wire or, as shown in FIG. 13D, coil 19. The outer tubular member 30 moves forward to bring the loops together and apart as shown in FIG. 13C. The grasping assembly can also combine loops with jaws as shown in FIG. 13C. The loop would encircle a larger surface area of the object to be removed whereas the jaws would clamp onto the object to be removed. The arrangement of loops and jaws provides an increase of total surface area than jaws alone, but allows the object to be grabbed into and held. It should be noted that the embodiment of FIGS. 13A-D may be constructed with tubing having a wall with perforations for releasing a fluid within the tubing as disclosed in the embodiments of FIGS. 12A-12E.

Loops 405 may be formed from ribbon or wire. Loops 405 may be constructed of various materials having suitable strength, elasticity and memory for use in engaging and removing an object such as thrombus from a body lumen, particularly a cerebral vessel. However, loops are generally constructed from a metal which may be for example platinum (or alloys thereof), stainless steel, super-elastic nickel-titanium alloy, or high strength cobalt-chromium-molybdenum alloys.

FIGS. 14A-14D illustrate an alternative intracorporeal grasping system 500. A grasping assembly 501 may be formed in a web configuration such with webbed jaws. Webbed jaws provide stronger and increased coverage or encapsulation of the object to be removed than jaws without webs. The web may be constructed by attaching fiber or welding metallic strands to the individual grasping mechanism.

Figure 14A:
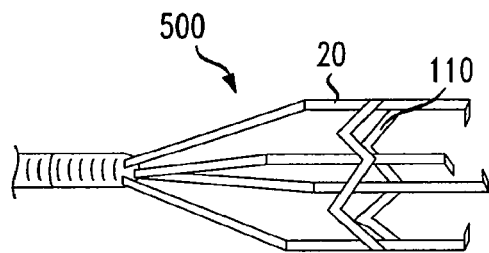
FIGS. 14A-14E illustrate an alternative embodiment of a grasping system according to the teaching of the present invention.
Figure 14B:
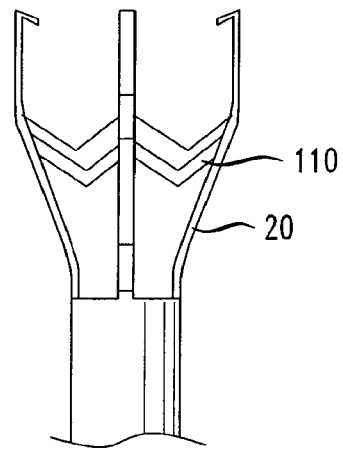
Figure 14C:
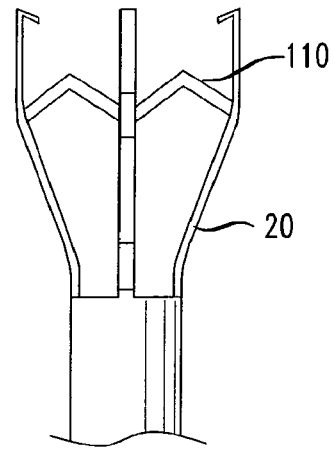
Figure 14E:
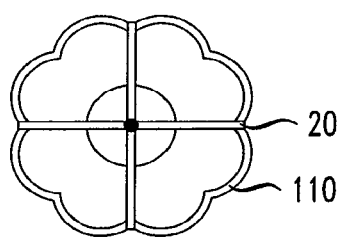
Figure 14D:
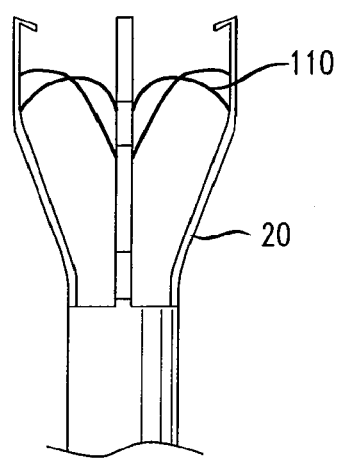

The webs may be formed from ribbon as shown in FIGS. 14A-14C or wire as shown in FIG. 14D. The webs connect between jaws in a concave or convex manner as shown in FIG. 14B or 14C as are flexible to bend or stretch based on the movement of elongate member 14 into and out of tube 30.

Webs 110 can be attached during jaw formation, or they can be formed from the same piece of the jaws. The jaws can be made in a manner similar to a laser cut stent, so webs and jaws are one piece (cut tubing). Webs 110 may be constructed of various materials having suitable strength, elasticity and memory for use in engaging and removing an object such as thrombus from a body lumen, particularly a cerebral vessel. However, loops are generally constructed from a metal which may be for example platinum (or alloys thereof), stainless steel, super-elastic nickel-titanium alloy, or high strength cobalt-chromium-molybdenum alloys.

Figure 15A:
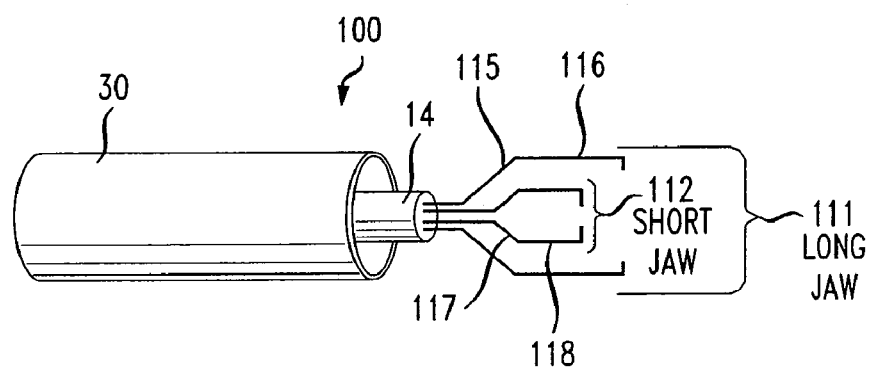
FIGS. 15A-15B illustrate an alternative embodiment of a grasping system according to the teaching of the present invention.
Figure 15B:
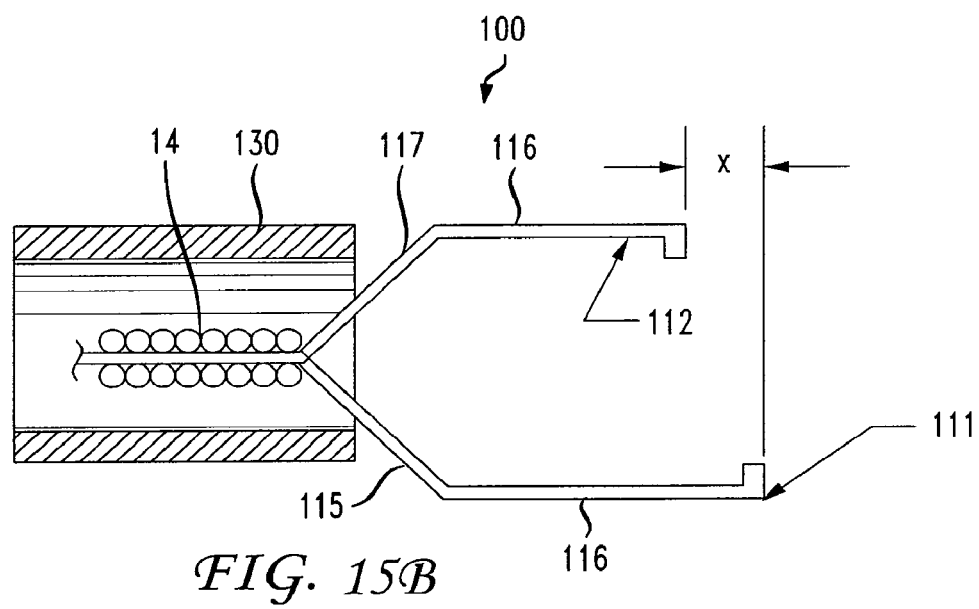

FIGS. 15A-15B illustrate an alternative intracorporeal grasping system 100. The proximal arm sections and distal arm sections may have different lengths and can be offset for different specific intended procedures. As shown in FIG. 15A, opposing pairs of jaws 111 comprising proximal arm 115 section and distal arm section 116 having a longer longitudinal length (as measured from the distal end 16 of core member 14) than the longitudinal length opposing pairs of jaws 112 comprising proximal arm 117 section and distal arm section 118. Hence, the jaws 111 and 112 are offset from each other a longitudinal distance denoted as "delta X" or simply "X". The jaws 111 and 112 are offset from each other such that when tube 30 slidably engages the periphery of the jaws, the longer jaws 111 will contract before the shorter jaws 112. The offsetting feature of the jaws enables the jaws 111, 112 to clamp down at different times during longitudinal movement of the lumen 30 towards to the jaws 111, 112. Each jaw may be offset relative to the other jaws or pairs of jaws may be offset relative to other pairs of jaws. Nevertheless, other configurations are possible for the grasping system 100.

Figure 16A:
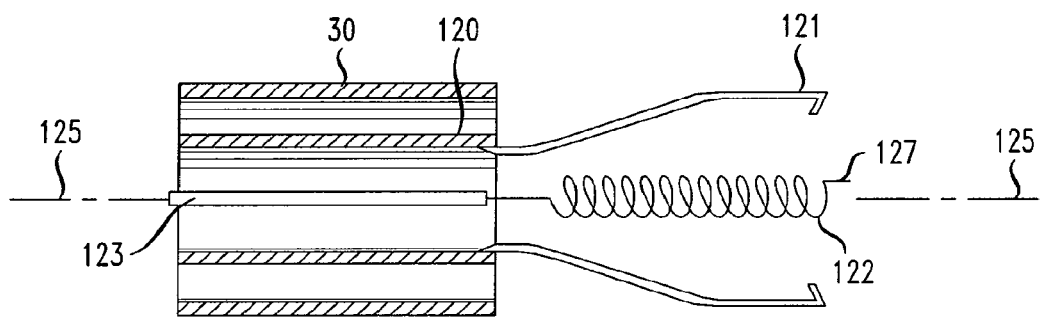
FIGS. 16A-16C illustrate an alternative embodiment of a grasping device according to the teaching of the present invention.
Figure 16B:
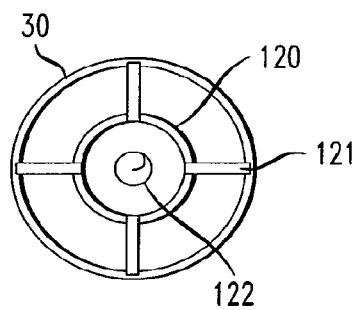
Figure 16C:
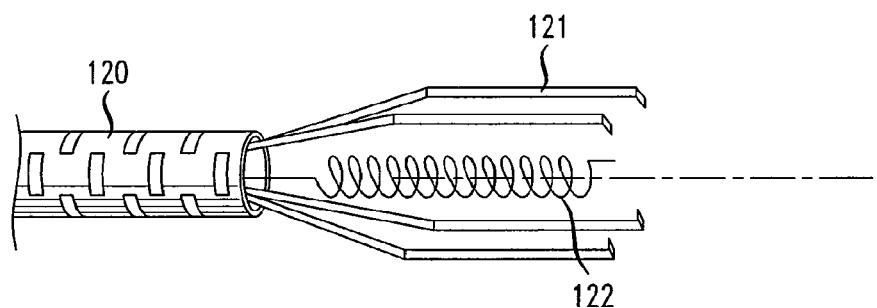
Figure 17A:
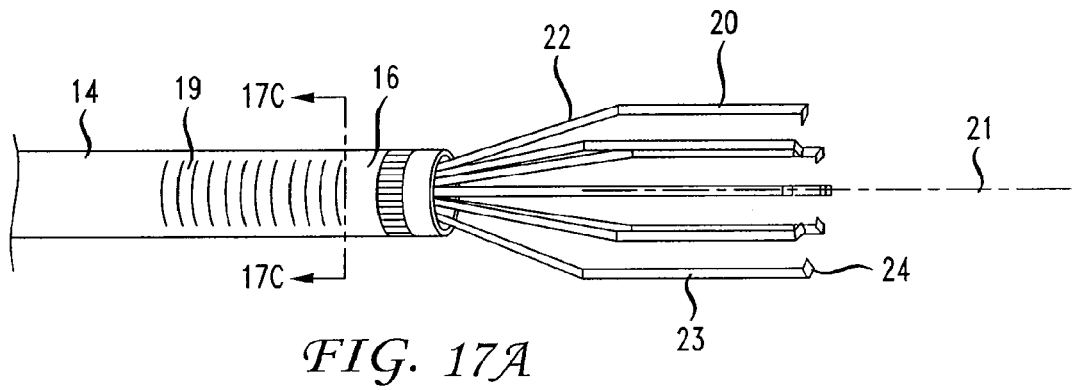
FIGS. 17A-17D illustrate an alternative embodiment of a grasping device according to the teaching of the present invention.
Figure 17B:
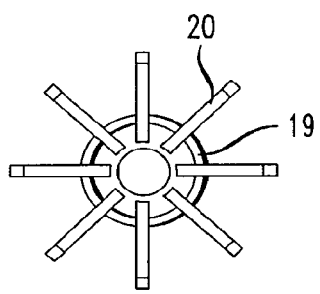
Figure 17C:
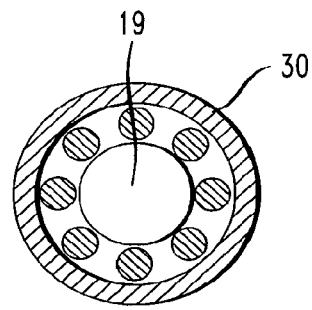
Figure 17D:
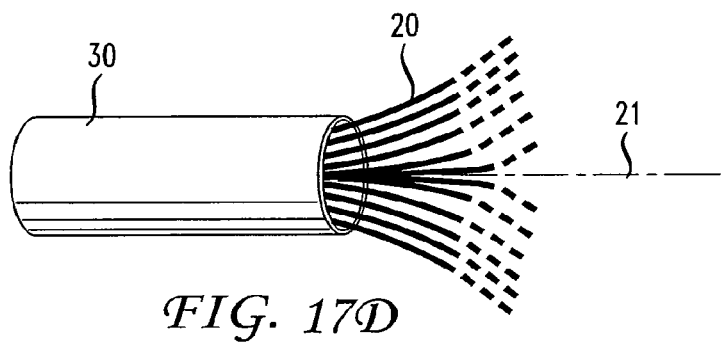

FIGS. 16A-16C illustrate an alternative intracorporeal grasping system. Elongate core member 14 comprises an elongate tube 120 positioned within tube 30. Jaws 121 are attached to or formed at the distal end of elongate tube 120 as shown in FIG. 16A such that when core member 14 is withdrawn into tube 30, the jaws clamp down on an object to be removed. Referring to FIG. 16C, the elongated tube 120 may have a multi-flexion configuration that has separate regions of different flexions that each correspond to the flexibility, or lack thereof, for improved transluminal manipulation. This multi-flexion regional configuration provides adaptability for a practitioner to reduce steps for accessing or grasping an object or customize the access in body lumens to increase patient comfort. This feature incorporates the features of grasping system 10 as discussed in the foregoing.

Generally concentrically located within elongate tube 120 is elongate cylindrical member 123 having a spiral-shaped member 122 (e.g., corkscrew-like member) attached to a distal end thereof The elongate cylindrical tube 120 may be tapered in one embodiment. The member 123 may have various dimensional characteristics. In one example, the outer diameter ("OD") at the distal end of the cylindrical member 123 may be 0.012 inches. The spiral-shaped member 122 may be formed with a wire having an OD about may be 0.008 inches to 0.010 inches. Nevertheless, other configurations and dimensions are possible within the scope of the invention. The spiral shaped member 122 may be formed integrally with the distal end of the cylindrical member 123.

The spiral-shaped member 122 engages into an object to be removed (e.g., clot 50) via rotational movement about a longitudinal axis 125. The distal end 127 of the spiral-shaped member 122 includes sharpen tip for penetrating into the interior of the clot during the rotational movement. Once the clot is engaged by member 122, then the elongate tube 120 is withdrawn into tube 30. Elongate tube 120 is preferably flexible. The jaws 121 may be attached to the inside or outside of the tube 120 or may be formed from the tube itself as disclosed in alternative embodiment herein (e.g., FIGS. 8A-8C, and 9A-9C). Nevertheless, other configurations and arrangements are possible.

FIGS. 17A-17D illustrate an alternative embodiment of a grasping device according to the teaching of the present invention. Jaws 20 are made of wire having a generally circular cross-section. It was discovered that the circular cross-section of the jaws allows the jaws to be easily inserted and aligned evenly in coil 19 (See FIG. 17A) or other concentric tube or guidewire. The jaws are more flexible than conventional jaws, which allow a better grip on the object to be removed.

At least six, preferably eight to twelve, wire jaws 20 are integrally secured to the distal end 16 of the elongate core member 14 and disposed about the longitudinal axis 21. Outer tubular body 30 (see FIG. 1) surrounds the jaws 20 and coil 19.

Each jaw 20 has a proximal arm section 22 secured to the distal end 16 of the elongate core member 14. The proximal arm section 22 is inclined from the distal end 16 of the core member 14. The inclined proximal arm section 22 functions to aid in placing the jaws 20 of the grasping assembly 17 into a contracted or partially contracted configuration about the longitudinal axis 21 by the force applied to the inclined section by advancement of the distal end of the delivery catheter 12 and has a length selected to provide the desired radial spacing between the distal arm sections 23.

In operation, the jaws 20 extend along a length of the object to be removed and are retracted by retracting elongate core member 14. As the jaws are being retracted, they are forced to bite down on the object and then pull the object into tubular body 30.

Jaws 20 may be constructed of various materials having suitable strength, elasticity and memory for use in engaging and removing an object such as thrombus from a body lumen, particularly a cerebral vessel. However, jaws 20 are generally constructed from a metal which may be for example platinum (or alloys thereof), stainless steel, super-elastic nickel-titanium alloy, or high strength cobalt-chromium-molybdenum alloys.

While the arrangements and various embodiments described are believed to be well suited for engaging and removing various objects from various body spaces, the primary basis underlying many of the beneficial features herein described are for the purpose of accessing distal, tortuous cerebral vessels for removal of thromboembolism in the treatment of strokes, as previously described above. Nevertheless, other purposes of devices can be advantageously applied to other biological organisms.

There are any number of alternative arrangement for practicing techniques and aspects herein. For example, an intracorporeal grasping device may include a tubular member for entering a lumen of a human body and the tube member having a distal end portion. An elongated core member is disposed with the interior cavity of the tubular member for rotational or slidably movement within the tubular member and the elongated core member having a proximal end portion and a distal end portion. A grasping configuration is provided for capturing an object (e.g., clot or debris) therein in which the grasping configuration is formed by at least one movable jaw attached to the distal end portion of the elongated core member and a length portion of the distal end portion of the tube member. The grasping configuration may include unitarily formed plurality of movable jaws attached to the distal end portion of the elongated core member. Further, the grasping configuration may be formed by a plurality of loop members attached to the distal end portion of the elongated core member.

In another example, an intracorporeal grasping device includes a tubular member for entering a lumen of a human body and the tubular member having a distal end portion. An elongated core member being disposed with the tubular member and the elongated core member having a proximal end portion and a distal end portion. A grasping configuration is provided for capturing an object therein, in which the grasping configuration is formed by at least one spiral member having a distal tip for penetrating an object to be removed from a human body lumen. The device has the spiral member provided at the distal end portion of the elongated core member. The grasping configuration can be formed by at least one web member for retaining an object to be removed from a human body lumen, the web member being provided at the distal end portion of the elongated core member.

There are any number of alternative combinations for defining the invention, which incorporate one or more elements from the specification, including the description, and drawings and claims, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations.

What is claimed is:

1. An intracorporeal grasping device, comprising:
   an elongated member having a proximal end and a distal end;
   a grasping assembly comprising a proximal portion and a distal portion, the proximal portion being attached to the distal end of the elongated member, the distal portion comprising a plurality of jaws and strands, each of the strands having an entire length extending between members of a respective pair of jaws, being permanently attached to the members of the respective pair of jaws at axial locations proximal to terminal distal ends of the members of the respective pair of jaws, and being oriented concave along the entire length and toward the terminal distal ends;
   wherein the jaws comprise object engaging elements extending radially inward from the terminal distal ends toward a longitudinal axis of the device, the object engaging elements being configured to be placed alongside an object for engaging and removing the object from a body lumen.

2. The device of claim 1, wherein the proximal portion is tapered.

3. The device of claim 1, wherein the proximal portion is inclined relative to the member.

4. The device of claim 1, wherein the jaws comprise super-elastic material.

5. The device of claim 1, wherein the strands are formed from a laser cut tube and integrally connected to the jaws.

6. The device of claim 1, wherein the object is a thrombus.

7. The device of claim 1, wherein the member is provided with variable bending flexibility along a predetermined length.

8. The device of claim 7, wherein the flexibility is provided by a plurality of spaced apart circumferential slots along the member.

9. The device of claim 1, wherein the distal portion of the grasping assembly comprises an angled tip.

10. The device of claim 1, wherein each of the strands has a first end and a second end, the first and second ends being attached to the members of the respective pair of jaws at an axial location along the longitudinal axis of the device.

11. The device of claim 1, wherein the members of the respective pair of jaws are circumferentially adjacent to each other.

12. A system for retrieving an object within the human vasculature, comprising: the device of claim 1; and
a delivery catheter having a proximal end and a distal end and a lumen configured to receive said device.

13. The system of claim 12, further comprising a vacuum to provide negative pressure to the vasculature.

14. A method of retrieving an object within the human vasculature comprising:
advancing a delivery catheter into the vasculature, the delivery catheter having a lumen configured to receive the device of claim 1;
delivering the device of claim 1 from the lumen, said delivering comprising separating the delivery catheter from the device so that at least a portion of the grasping assembly expands outside of the delivery catheter into contact with the object alongside the object;
removing the object from the vasculature by retracting the device with the object engaged therewith from the vasculature.

15. The method of claim 14, further comprising applying vacuum while removing the object.

* * * * *